United States Patent
Yoshida et al.

(10) Patent No.: US 8,086,411 B2
(45) Date of Patent: Dec. 27, 2011

(54) SYSTEM FOR PROVIDING ANIMAL TEST INFORMATION AND METHOD OF PROVIDING ANIMAL TEST INFORMATION

(75) Inventors: Takashi Yoshida, Akashi (JP); Yoichi Nakamura, Kobe (JP)

(73) Assignee: Sysmex Corporation, Kobe (JP)

( * ) Notice: Subject to any disclaimer, the term of this patent is extended or adjusted under 35 U.S.C. 154(b) by 449 days.

(21) Appl. No.: 12/316,306

(22) Filed: Dec. 11, 2008

(65) Prior Publication Data

US 2009/0254284 A1    Oct. 8, 2009

(30) Foreign Application Priority Data

Dec. 12, 2007  (JP) ................................. 2007-320460
Dec. 12, 2007  (JP) ................................. 2007-320927

(51) Int. Cl.
*G06F 19/00*  (2011.01)
*G01N 33/48*  (2006.01)

(52) U.S. Cl. ................ 702/19; 702/21; 702/23; 702/27; 702/30; 702/31; 702/32; 702/122; 702/127; 702/182; 702/188

(58) Field of Classification Search .................... 702/19, 702/21, 23, 27, 30–32, 122, 127, 182, 183, 702/188
See application file for complete search history.

(56) References Cited

U.S. PATENT DOCUMENTS

| | | | |
|---|---|---|---|
| 6,391,263 B1 | 5/2002 | Mishima et al. | |
| 6,629,060 B2 | 9/2003 | Okuno et al. | |
| 7,085,669 B2 * | 8/2006 | Isami | 702/127 |
| 2005/0053521 A1 | 3/2005 | Hirayama | |
| 2005/0102166 A1 | 5/2005 | Tohma | |

\* cited by examiner

*Primary Examiner* — Sujoy Kundu
(74) *Attorney, Agent, or Firm* — Brinks Hofer Gilson & Lione

(57) ABSTRACT

A system for providing animal test information is disclosed that comprises: test devices; and a central device communicably connected to the test devices, wherein each of the terminal test devices comprises: an input receiving section for receiving input of attribution information of a sample; a measurement section for measuring the sample and acquiring a measurement result; an information transmitting section for transmitting a data set of the attribution information and the measurement result to the central device, wherein the central device comprises: an information receiving section for receiving the data set; a data storage for storing a plurality of the data set; a standard value calculation section for calculating a standard value to be used for determining a treatment of an animal, based on a plurality of the measurement result included in a plurality of the data set which have common attribution information.

20 Claims, 19 Drawing Sheets

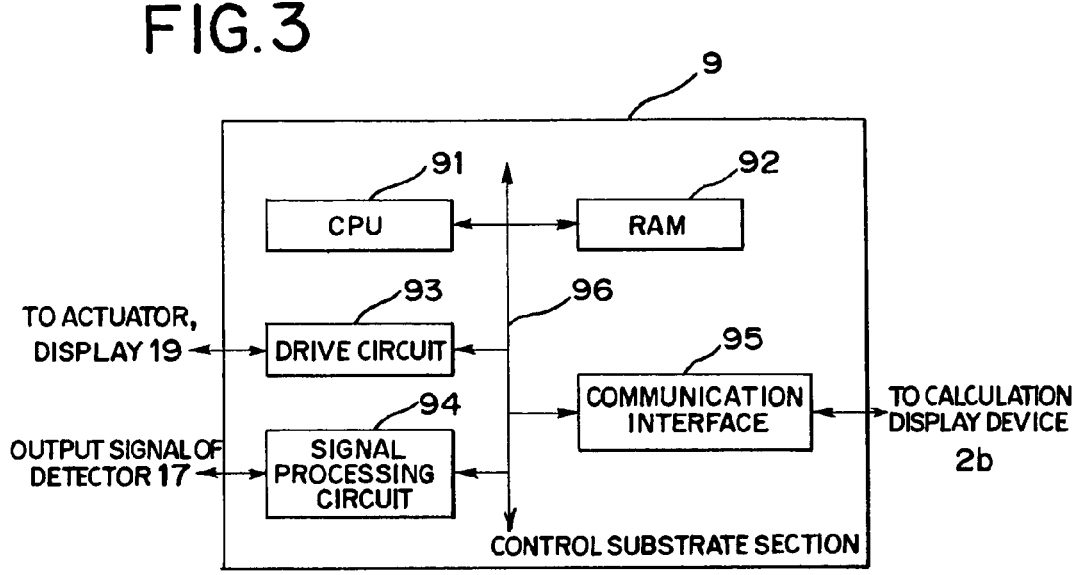
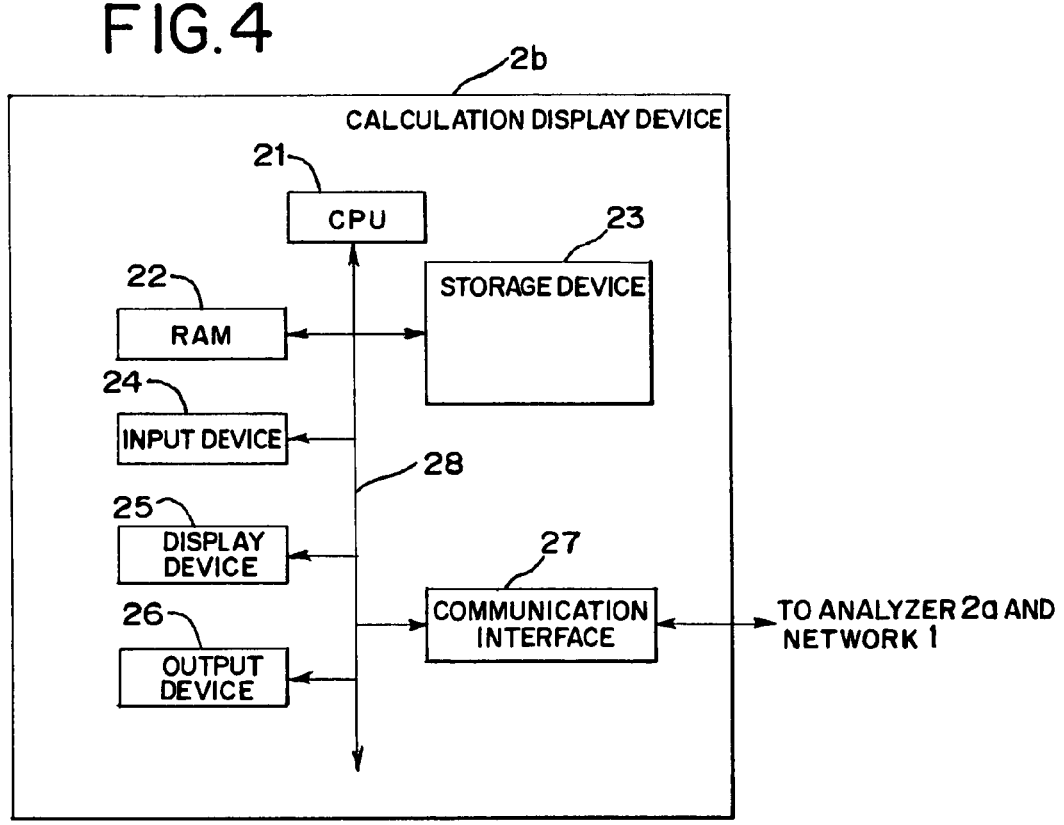

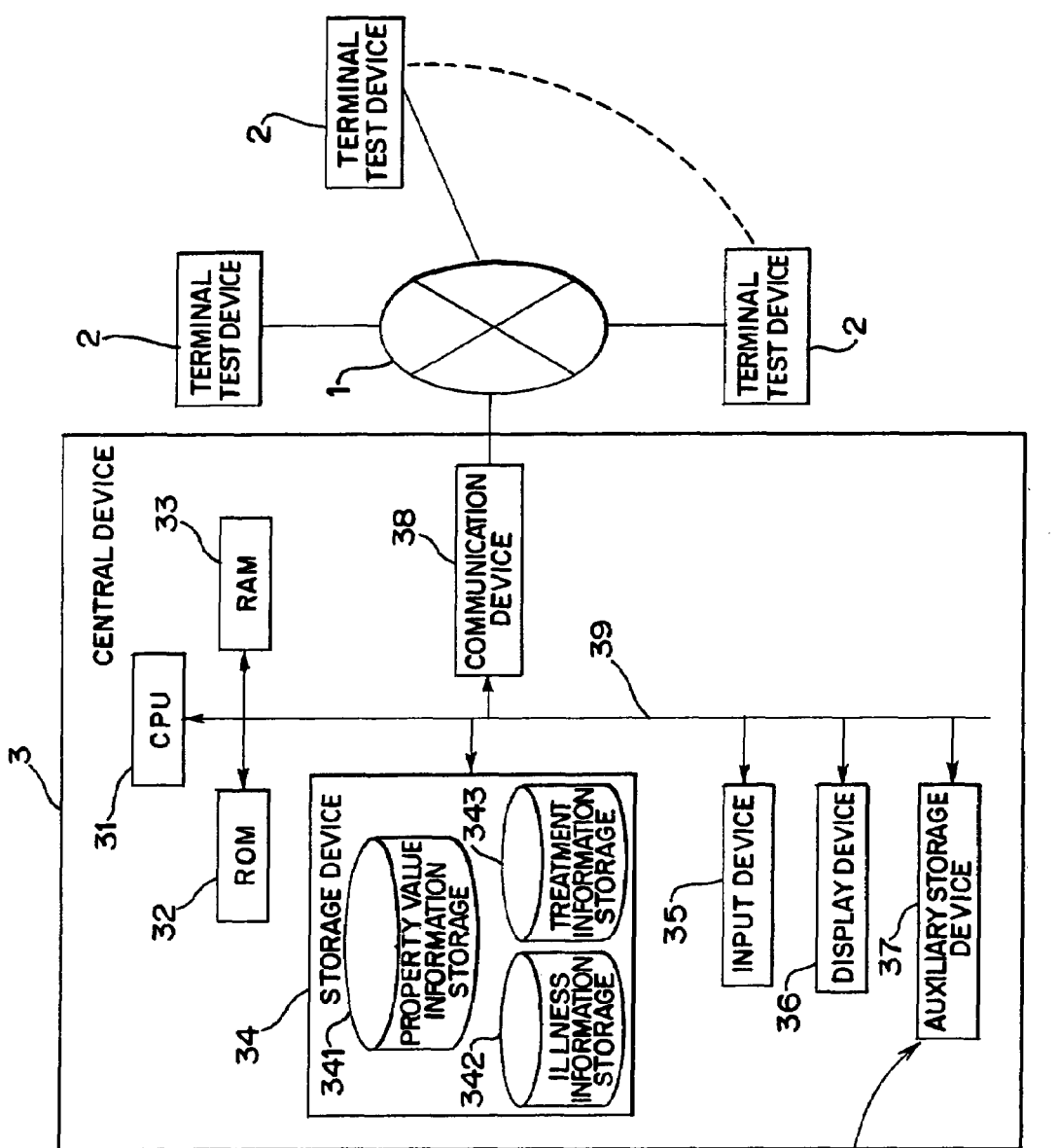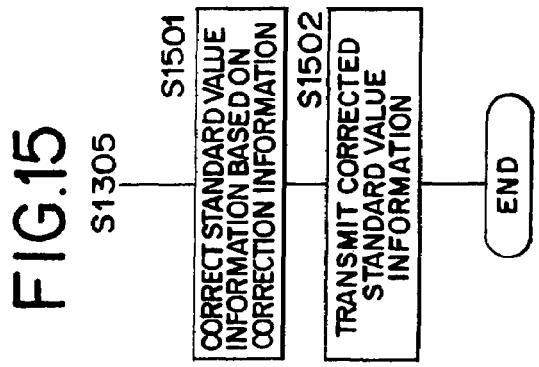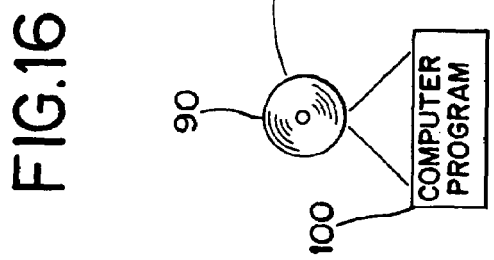

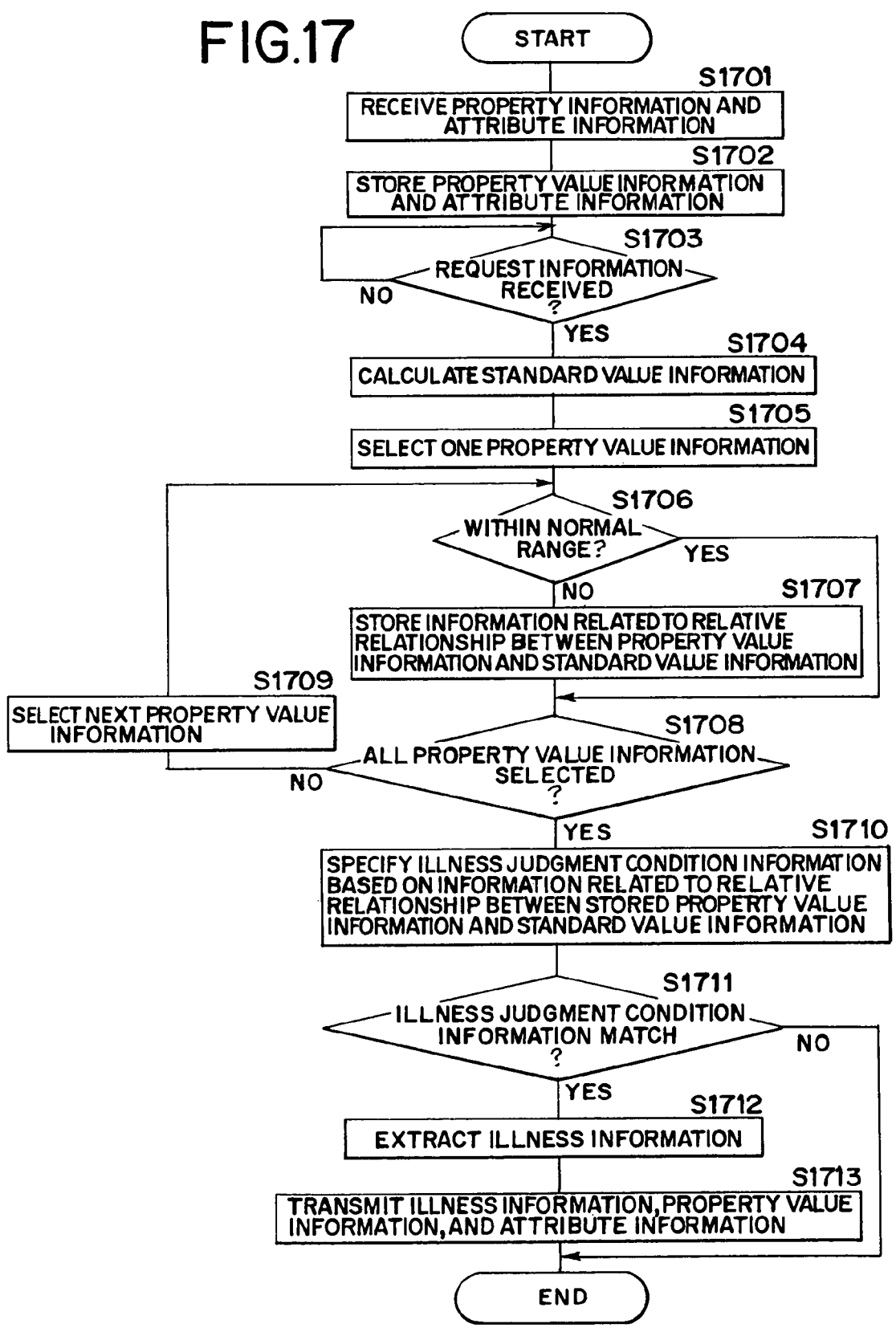

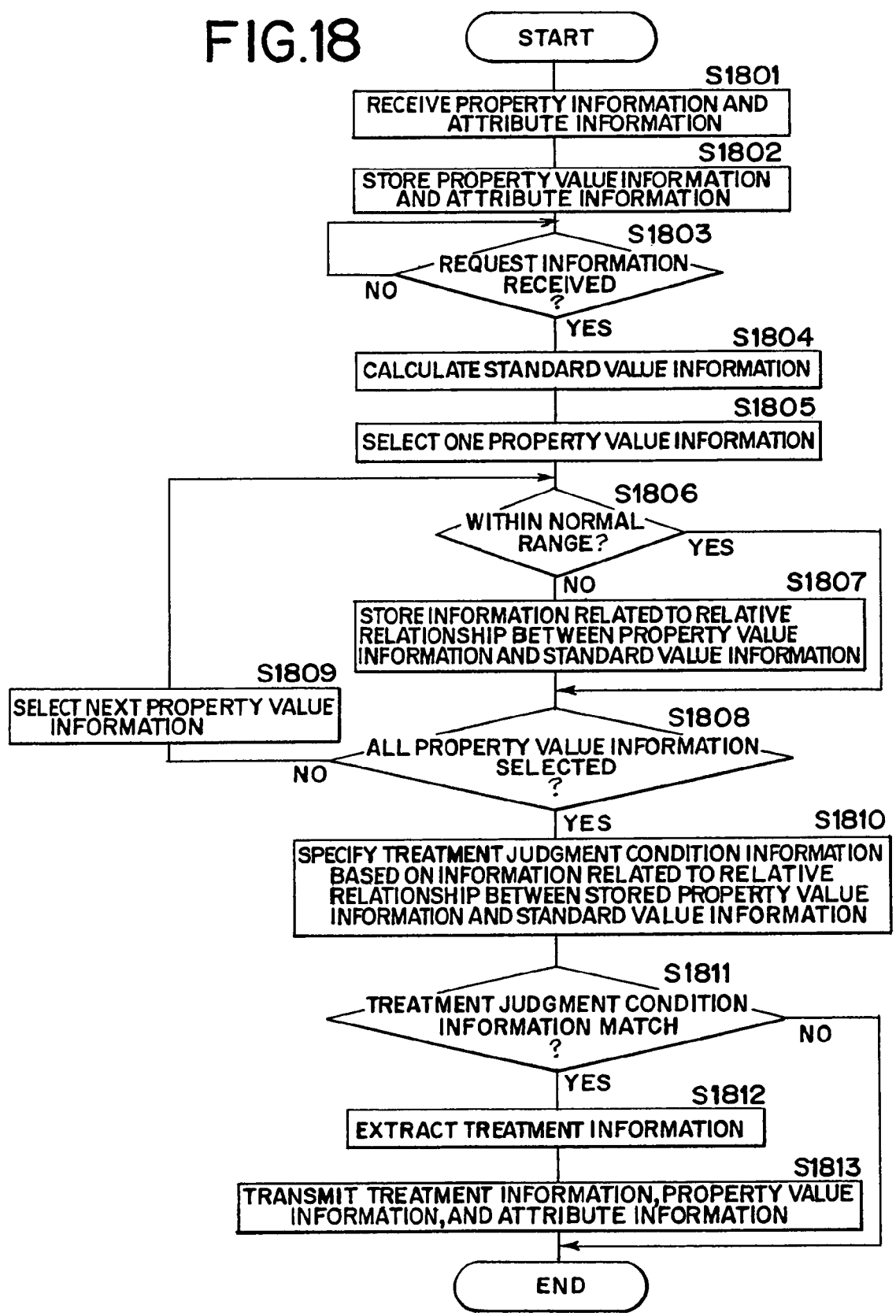

Fig. 19

```
Animal species:   dog
Period:           October 1, 2007 to November 30, 2007

Date      RBC   WBC   PLT
2007/10/1    xxx   xxx   xxx
2007/10/1    xxx   xxx   xxx
    xxx      xxx   xxx   xxx
    xxx      xxx   xxx   xxx
    xxx      xxx   xxx   xxx
    xxx      xxx   xxx   xxx
```

Fig. 20

| Animal species: | dog | | | | | |
|---|---|---|---|---|---|---|
| Period: | October 1, 2007 to November 30, 2007 | | | | | |
| Date | RBC | Correction value | WBC | Correction value | PLT | Correction value |
| 2007/10/1 | xxx | xxx | xxx | xxx | xxx | xxx |
| 2007/10/1 | xxx | xxx | xxx | xxx | xxx | xxx |
| xxx | xxx | xxx | xxx | xxx | xxx | xxx |
| xxx | xxx | xxx | xxx | xxx | xxx | xxx |
| xxx | xxx | xxx | xxx | xxx | xxx | xxx |
| xxx | xxx | xxx | xxx | xxx | xxx | xxx |

SYSTEM FOR PROVIDING ANIMAL TEST INFORMATION AND METHOD OF PROVIDING ANIMAL TEST INFORMATION

RELATED APPLICATIONS

This application claims priority under 35 U.S.C. §119 to Japanese Patent Application No. 2007-320460 filed Dec. 12, 2007, and Japanese Patent Application No. 2007-320927 filed on Dec. 12, 2007, the entire contents of which are hereby incorporated by reference.

TECHNICAL FIELD

The present invention relates to a system for providing animal test information capable of providing standard value information used to determine the treatment of animals in the animal test, a central device, a method of providing animal test information, and a computer program. The present invention also relates to a system for providing animal test information for managing test results obtained in the animal test device, a central device, an animal test device, a method of providing animal test information, and a computer program.

BACKGROUND

In medical institutions targeted on animals such as veterinary hospitals, various clinical tests are conducted, similar to medical institutions targeted on humans. A clinical test system dedicated to animals is introduced in some medical institutions targeted on animals, but since the component of the specimen such as the size of red blood cells and the concentration greatly differs depending on the animal species in the case of animals, the analyzing conditions such as the type of analyzing program, measurement sensitivity, reaction time, measurement reagent and the like need to be changed according to the animal species.

Since changing and setting the analyzing conditions for every animal species are troublesome to the worker, test can be carried out in an optimum analyzing condition for every animal species without performing a troublesome operation by selecting an animal species (dog, cat, monkey, and the like) to be tested and analyzing the test data in the analyzing condition corresponding to the selected animal species in U.S. Pat. No. 6,391,263.

US Patent Application Publication No. 2005/0053521 discloses an analyzing system capable of easily changing the measurement mode according to the animal species, and capable of outputting the analysis result in the optimum analyzing condition for every animal species by changing the analyzing condition corresponded by measurement mode.

In medical institutions targeted on animals such as veterinary hospitals as well, a sample is analyzed in an analyzer, and the obtained analysis result is compared with a standard value used to determine the treatment such as no treatment is required as the subject is healthy, re-test is necessary, medication is necessary, surgery is necessary, and the like to thereby determine the treatment, similar to the medical institutions targeted on humans. However, in clinical tests targeted on animals, the absolute number of test data is smaller than the case of being targeted on humans, and the variation in the component of the specimen is large depending on animal species, or even on the same animal species, on attribute information such as breed, sex, age and the like. Therefore, it is difficult to find an objective base with respect to the standard value used to determine the treatment, and there is a problem that the treatment needs to be determined relying on the intuition and the experience of the doctor present at the clinical test.

In rare animals barely handled in veterinary hospitals, it is more difficult to judge whether or not the standard value is reliable.

The analyzer for animals is generally used stand alone without being connected to other computers, but U.S. Pat. No. 6,391,263 discloses connecting the analyzer for animals and the host computer by way of a network.

Connecting an analyzer for humans and another computer by way of a network is also known. For instance, U.S. Pat. No. 6,629,060 discloses a remote support system in which an analyzer for humans and a server of a provider providing the system are connected by way of a network. US Patent Application Publication No. 2005/0102166 discloses a clinical test system in which an analyzer for humans and a server in a facility for conducting test by such analyzer are connected by way of a network.

Furthermore, U.S. Pat. No. 7,085,669 discloses an analysis data providing system in which an analyzer and a management device of a provider providing the system are connected by way of a network. U.S. Pat. No. 7,085,669 also discloses transmitting information indicating biological type of dogs, cats, and the like from the measurement device to the server.

The number of people having pets is increasing in recent years. The number of tests of the sample and the type of measurement items are also increasing therewith in veterinary hospitals. However, since the analyzer for animals is generally used stand alone, the storage capacity of the measurement result is relatively small, and the measurement results are printed out and saved in the present situation. Furthermore, as the sample of the animal has different components depending on the type of animal, when the sample of a certain animal species is tested, the test result of another sample of the relevant animal species is sometimes desirably referenced. In the past, the necessary measurement result needs to be found from the numerous measurement results that are printed out and saved, which task is very troublesome.

Moreover, a system in which the analyzer and the server are connected by way of a network is known, as described above, but such system does not solve the problems specific to the test of the sample of animals.

For example, U.S. Pat. No. 6,391,263 discloses connecting the analyzer for animals and the host computer by way of the network, but the host computer merely stores an animal species table in which the analyzable animal species and the ID for specifying the relevant animal species are corresponded, and the patent does not describe at all how to manage the measurement result (property value) obtained by the analyzer for animals.

In U.S. Pat. No. 6,629,060, the measurement result of precision management substance is transmitted from the analyzer to the server, and transmitting the measurement result of the sample is not described at all. The measurement result of the sample of humans is personal information, and thus transmitting such information to an external server has a large risk of information leakage, and the desire to transmit the measurement result of the sample of humans to the external server is very small.

In US Patent Application Publication No. 2005/0102166, the measurement result of the sample of humans is transmitted to the server in the facility. However, this system is targeted on the sample of humans, and the description on managing the measurement result of the sample of animals is not made at all. In particular, the information on the animal species becomes important in managing the measurement result since the sample of animals has different components depending on the type of animals, but this aspect is not described at all in US Patent Application Publication No. 2005/0102166.

In U.S. Pat. No. 7,085,669, transmitting information indicating biological type of dogs, cats and the like from the measurement device to the server is disclosed. However, the data transmitted from the measurement device to the server in this system is not the final measurement result to the user of the analyzer, but is the intermediate data, and a dedicated server for analyzing such intermediate data is necessary to obtain the final measurement result. Although the number of samples is increasing in recent years, the number of samples is very small in the test of animals compared to the test of humans, and thus it is not realistic to arrange an analysis dedicated server.

SUMMARY OF THE INVENTION

The scope of the present invention is defined solely by the appended claims, and is not affected to any degree by the statements within this summary.

A first system for providing animal test information embodying features of the present invention includes: test devices for measuring samples obtained from animals; and a central device communicably connected to the test devices, the central device being for collecting and processing measurement results acquired by the test devices, wherein each of the terminal test devices comprises: an input receiving section for receiving input of attribution information of a sample; a measurement section for measuring the sample and acquiring a measurement result; an information transmitting section for transmitting a data set of the attribution information and the measurement result of the sample to the central device, wherein the central device comprises: an information receiving section for receiving the data set from each of the test devices; a data storage for storing a plurality of the data set; a standard value calculation section for calculating a standard value to be used for determining a treatment of an animal, based on a plurality of the measurement result included in a plurality of the data set which have common attribution information.

A first method of providing animal test information with a system comprising test devices for measuring samples obtained from animals and a central device communicably connected to the test devices, the central device being for collecting and processing measurement results acquired by the test devices, embodying features of the present invention includes steps of: receiving input of attribution information of a sample in each of the test devices; measuring the sample and acquiring a measurement result in each of the test devices; transmitting a data set of the attribution information and the measurement result from each of the test devices to the central device; receiving the date set from each of the test devices in the central device; storing a plurality of the data set in the central device; and calculating a standard value to be used for determining a treatment of an animal, based on a plurality of the measurement result included in a plurality of stored data set which have common attribution information.

A second system for providing animal test information embodying features of the present invention includes: test devices for measuring samples obtained from animals; and a central device communicably connected to the test devices, the central device being for collecting and processing measurement results acquired by the test devices, wherein each of the test devices comprises: an input receiving section for receiving input of attribution information indicating animal species or breed of the animal serving as a collecting source of a sample, a measurement section for measuring the sample and acquiring a measurement result, and an information transmitting section for transmitting a data set of the attribution information and the measurement result to the central device, wherein the central device comprises: an information receiving section for receiving the data set from each of the test devices, a data storage for storing a plurality of the data set, and an information output section for outputting the measurement result and the attribute information included in the data set stored in the data storage.

A second method of providing animal test information with a system comprising test devices for measuring samples obtained from animals and a central device communicably connected to the test devices, the central device being for collecting and processing measurement results acquired by the test devices, embodying features of the present invention includes steps of: receiving input of attribution information indicating animal species or breed of the animal serving as a collecting source of a sample in each of the test devices, measuring the sample and acquiring a measurement result in each of the test devices, and transmitting a data set of the attribution information and the measurement result from each of the test devices to the central device, receiving the data set from each of the test devices in the central device, storing a plurality of the data set, and outputting the measurement result and the attribute information included in the data set.

BRIEF DESCRIPTION OF THE DRAWINGS

FIG. 3 is a block diagram showing a configuration of a control substrate section of the analyzer;

FIG. 4 is a block diagram showing a configuration of a calculation display device of the terminal test device used in the system for providing animal test information according to the first embodiment of the present invention;

FIG. 15 is a flowchart showing another processing procedure of the CPU of the central device used in the system for providing animal test information according to the second embodiment of the present invention;

FIG. 16 is a block diagram showing a configuration of a system for providing animal test information according to a third embodiment of the present invention;

FIG. 17 is a flowchart showing a processing procedure of the CPU of the central device used in the system for providing animal test information according to the third embodiment of the present invention;

FIG. 18 is a flowchart showing another processing procedure of the CPU of the central device used in the system for providing animal test information according to the third embodiment of the present invention;

FIG. 19 is a view showing a browsing screen of the property value information displayed in the system for providing animal test information according to the first embodiment of the present invention;

FIG. 20 is a view showing a browsing screen of the property value information displayed in the system for providing animal test information according to the second embodiment of the present invention.

DETAILED DESCRIPTION OF THE PREFERRED EMBODIMENTS

In the present embodiment, an animal blood analyzer for analyzing the blood of an animal will be specifically described by way of example as a plurality of terminal test devices based on the drawings.

In the present embodiment, "property value information" refers to the information related to the property value that can be measured by physical and chemical method with respect to a sample, and is a wide concept that not only includes the measurement value itself but also information and the like related to the distribution of the measurement value. The "property value information" is the final measurement result of the sample, and does not refer to the intermediate data including light intensity data for creating a scattergram in the analyzer using a flow cytometer, scattered light intensity data in a blood coagulation measurement device, and the like. The number and the concentration of the component in the sample acquired using the light intensity data in the analyzer using the flow cytometer, and the coagulation time acquired using the scattered light intensity data in the blood coagulation measurement device correspond to the "property value information". The obtained property value information (initial property value) may be corrected according to the attribute information such as animal species, breed and sex of the animal serving as the collecting source of the sample to obtain the final property value. The "animal species" refers to the type of animal such as dogs and cats, and "breed" refers to the type such as bulldog, chihuahua, collie, and the like in dogs.

First Embodiment

Figure 1:
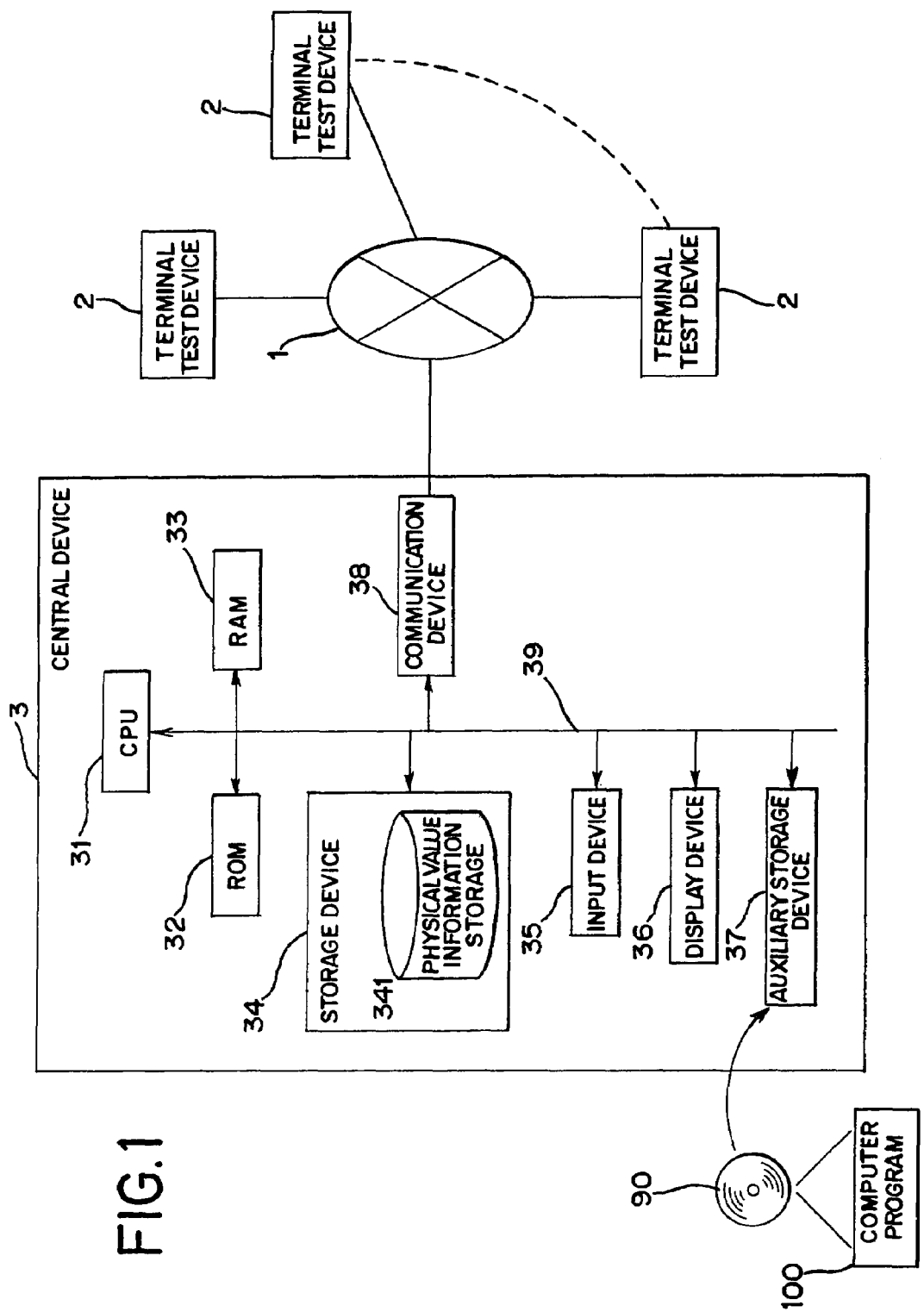
FIG. 1 is a block diagram showing a configuration of a system for providing animal test information according to a first embodiment of the present invention.

FIG. 1 is a block diagram showing a configuration of a system for providing animal test information according to a first embodiment of the present invention. As shown in FIG. 1, the system for providing animal test information according to the first embodiment is connected to a central device 3 and a plurality of terminal test devices 2, 2, . . . by way of a network 1 represented by Internet so as to be able to transmit and receive data.

The central device 3 is configured by at least a CPU (Central Processing Unit) 31, a ROM 32, a RAM 33, a storage device 34, an input device 35, a display device 36, an auxiliary storage device 37, a communication device 38, and an internal bus 39 for connecting the above-described hardware. The CPU 31 is connected to each hardware of the central device 3 by way of the internal bus 39, and controls the operation of each hardware and executes various software functions according to a computer program 100 stored in the storage device 34. The RAM 33 is configured by an SRAM, a flash memory, and the like, wherein a load module is developed in time of the execution of the computer program 100, and the RAM 33 stores temporary data and the like generated in time of the execution of the computer program 100. The computer program 100 may be obviously stored in the ROM 32 in advance.

The storage device 34 is configured by a built-in fixed storage device (hard disc) and the like. The computer program 100 stored in the storage device 34 is downloaded from a portable recording medium 90 such as DVD and CD-ROM which record information such as program and data by the auxiliary storage device 37, and developed from the storage device 34 to the RAM 33 and executed in time of execution. The computer program may be obviously downloaded from an external computer via the communication device 38.

The storage device 34 includes a property value information storage 341. The property value information storage 341 aggregates the information related to various property values measured by the user in the plurality of terminal test devices 2, 2, . . . and stores the same in correspondence to the attribute information.

The communication device 38 is connected to the internal bus 39, and can transmit and receive data with the external computer and the like by being connected to the external network 1 such as Internet, LAN, and WAN. That is, the storage device 34 is not limited to the configuration of being built in the central device 3, and may be an external recording medium such as external storage connected by way of the communication device 38.

The input device 35 is a data input medium such as keyboard and mouse. The display device 36 is a display device such as CRT monitor and LCD.

Figure 2:
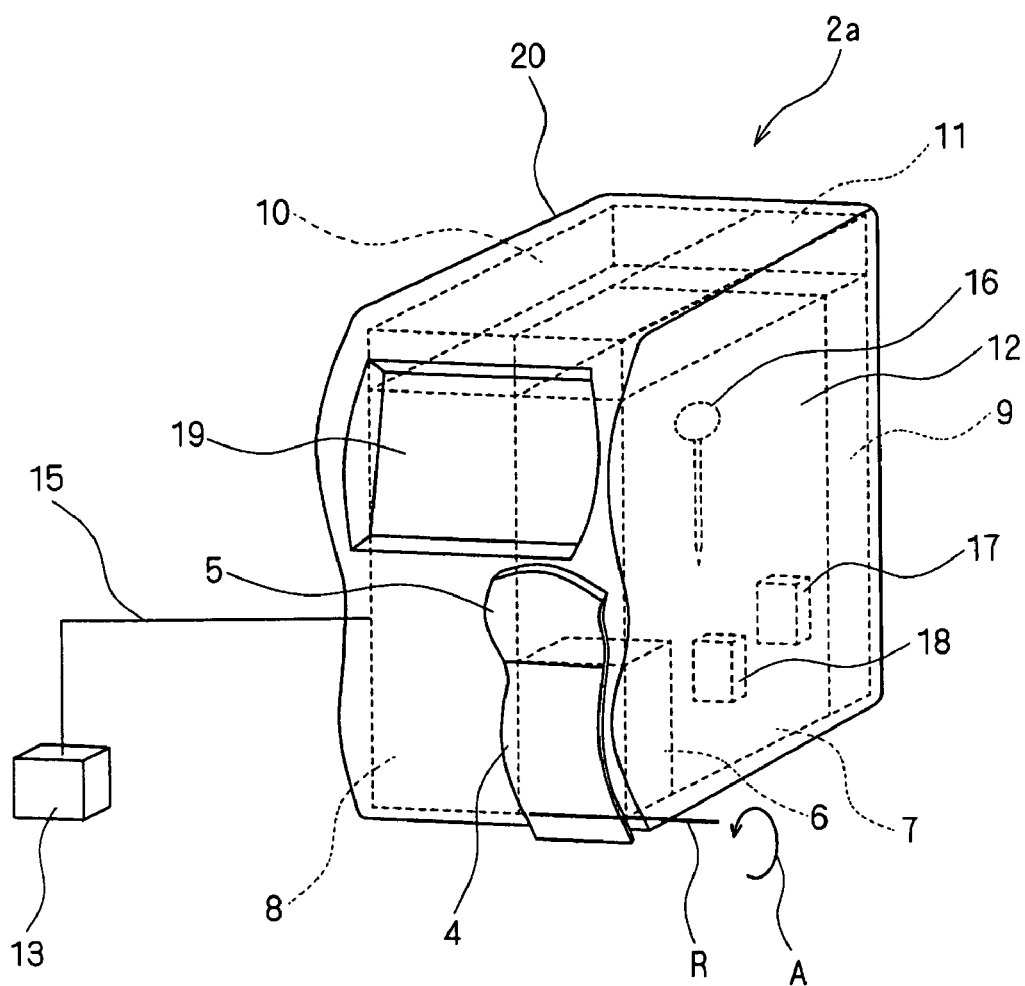
FIG. 2 is a perspective view schematically showing a configuration of an analyzer of a terminal test device used in the system for providing animal test information according to the first embodiment of the present invention.

In the first embodiment, the animal blood test apparatus is described as the terminal test device 2 by way of example. The terminal test device 2 is configured by an analyzer (e.g., blood cell counting device) and a calculation display device. FIG. 2 is a perspective view schematically showing the configuration of an analyzer 2a of the terminal test device 2 used in the system for providing animal test information according to the first embodiment of the present invention. As shown in FIG. 2, a housing 20 of the analyzer 2a accommodates a display 19, a control substrate section 9, a power supply section 10, a printer section 11, and a measurement section 12. The display 19 is a touch panel display that displays information and receives input from the user.

The measurement section 12 is configured by a sample set unit 6, a sample processing unit 7, and a fluid control unit 8. The sample set unit 6 has the upper surface opened, so that a sample container (container accommodating blood) can be set from the upper surface. A sample set panel 4 is attached to the sample set unit 6, and is positioned on the outer side of the housing 20.

A push button 5 is arranged on the outer side of the housing 20, and positions the sample set unit 6 by engaging with the sample set panel 4. When the push button 5 is pushed by the user, the engagement by the push button 5 is released, and the sample set unit 6 rotates by 45 degrees about an axis R in the A direction while being integrated with the sample set panel 4. The user can then set the sample container (container accommodating blood) from the upper surface of the sample set unit 6.

The user who has set the sample container can return the sample set unit 6 to the position shown in FIG. 2 by pushing the sample set panel 4 to rotate by 45 degrees. Similarly, when taking out the sample container from the sample set unit 6, the user can take out the sample container by pushing the push button 5 and rotating the sample set unit 6 by 45 degrees.

The sample processing unit 7 is configured by an aspiration mechanism 16, a detector 17, and a mix chamber 18. The aspiration mechanism 16 is a mechanism for aspirating the sample from the sample container set in the sample set unit 6, and injecting the sample to the detector 17 and the mix chamber 18, and includes an aspiration tube, and an actuator such as a motor.

The detector 17 is a detector of electrical resistance type, for example, and detects an electric signal based on the blood cells in the sample. A detector described in US Patent Application Publication No. 2002/0034824 specification may be used for the detector 17. The property value detected by the detector 17 is WBC (number of white blood cells), RBC (number of red blood cells), HCT (hematocrit value), and the like, and is output to the control substrate section 9 as an output signal.

The mix chamber 18 is a container whose upper part is opened for mixing the sample and a reagent. The fluid control unit 8 is connected with a reagent container 13 accommodating the reagent by way of a tube 15. The fluid control unit 8 includes a pump for transferring the reagent, and an actuator such as a motor for driving the pump, injects the sample, the reagent, and the like to the detector 17 and the mix chamber 18, and also discharges the same.

The control substrate section 9 controls the operation of each unit, acquires information related to the property value to be measured, and calculates the analysis result. The configuration of the control substrate section 9 will be hereinafter described. The power supply section 10 converts an alternating current (AC) received from a commercial AC to a direct current (DC), and supplies the same to the control substrate section 9 and the actuator such as the motor of each unit. A printer section 11 includes a printer for printing the analysis result and the like.

FIG. 3 is a block diagram showing a configuration of the control substrate section 9 of the analyzer 2a. As shown in FIG. 3, the control substrate section 9 is configured by at least a CPU 91, a RAM 92, a drive circuit 93, a signal processing circuit 94 for executing A/D conversion and the like, and a communication interface 95 capable of transmitting and exchanging data with outside via a network. The RAM 92 stores the computer program to be executed, the information related to the measurement result, and the like.

The drive circuit 93 controls the operation of the actuator such as the motor, the operation of the display 19, and the like in response to the command from the measurement operation program. The signal processing circuit 94 is a circuit for converting the output signal from the detector 17 to an analyzable digital signal. The communication interface 95 transmits the detected property value information to a calculation display device 2b via the network such as USB cable and LAN cable.

The CPU 91 is connected to each of the hardware of the control substrate section 9 via the internal bus 96, and controls the operation of each of the hardware, and also executes various software functions according to the computer program stored in the RAM 29. In other words, the CPU 91 executes the analyzing process and the like based on the signal digitalized in the signal processing circuit 94 and obtained in the detector 17, and transmits the property value information from the communication interface 95 to the calculation display device 2b via the network.

FIG. 4 is a block diagram showing a configuration of the calculation display device 2b of the terminal test device 2 used in the system for providing animal test information according to the first embodiment of the present invention. As shown in FIG. 4, the calculation display device 2b is configured by at least a CPU (Central Processing Unit) 21, a RAM 22, a storage device 23, an input device 24, a display device 25, an output device 26, a communication interface 27, and an internal bus 28 for connecting the hardware described above. The CPU 21 is connected to each of the hardware of the calculation display device 2 via the internal bus 28, and controls the operation of each of the hardware and executes various software functions according to the computer program stored in the storage device 23. The RAM 22 is configured by an SRAM, a flash memory and the like, wherein a load module is developed in time of the execution of the computer program, and the RAM 22 stores temporary data and the like generated in time of the execution of the computer program 100.

The storage device 23 is configured by a built-in fixed storage device (hard disc) and the like. The communication device 27 is connected to the internal bus 28, and can transmit and receive data with the external computer and the like by being connected to the analyzer 2a and the external network 1 such as Internet, LAN, and WAN. That is, the storage device is connected so as to be able to transmit and receive data with the central device 3 via the network 1 thereby transmitting the property value information to the central device 3 and receiving the information related to the result determination and the standard value information.

The input device 24 is a data input medium such as keyboard and mouse. The display device 25 is a display device such as CRT monitor and LCD, and graphically displays the information related to the result determination. The output device 26 is a printer such as a laser printer or an inkjet printer.

Figure 5:
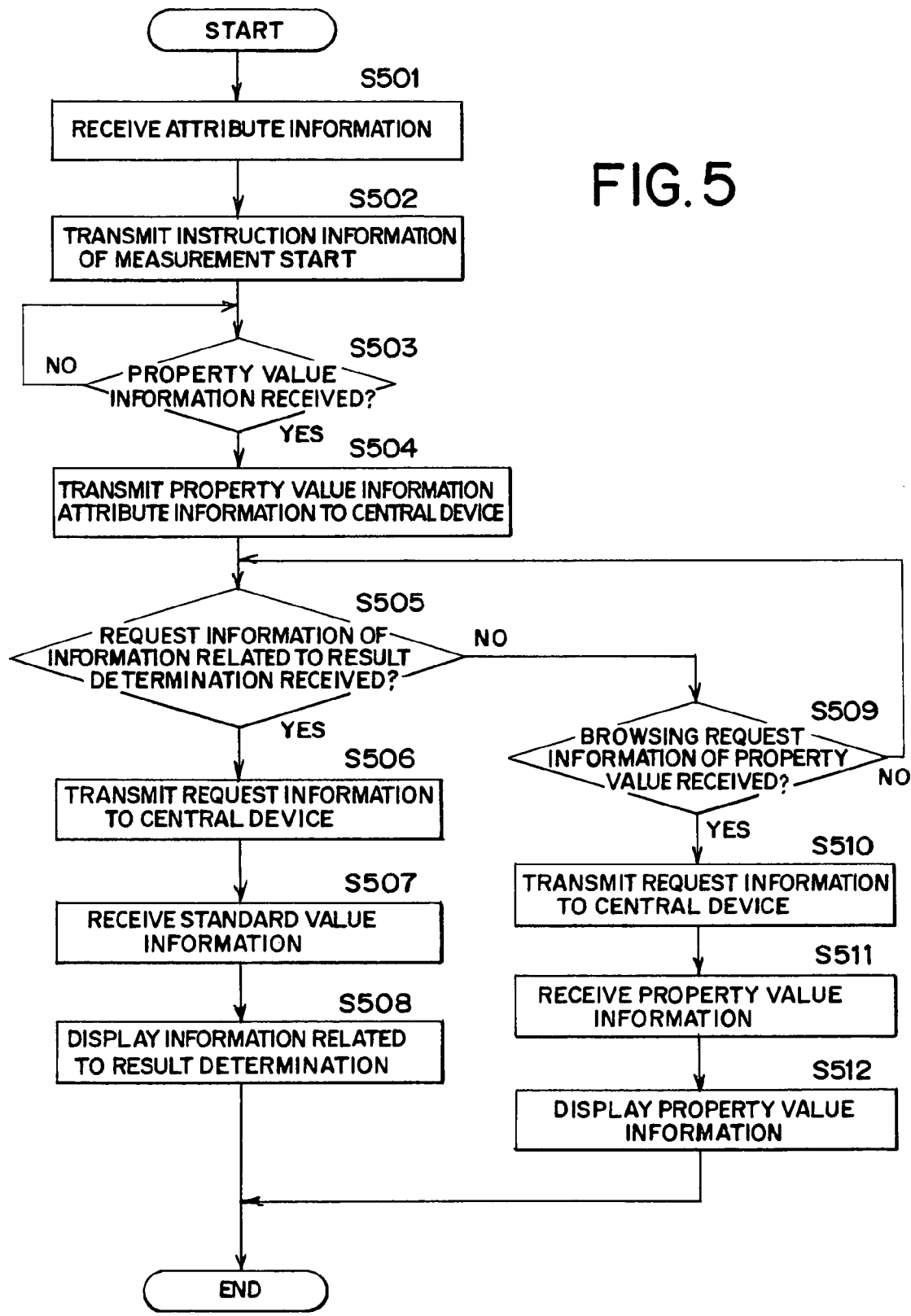
FIG. 5 is a flowchart showing a processing procedure of a CPU of the terminal test device used in the system for providing animal test information according to the first embodiment of the present invention.

The processing procedure in the terminal test device 2 and the central device 3 in the system for providing animal test information having the above-described configuration will now be described. FIG. 5 is a flowchart showing a processing procedure of the CPU 21 of the terminal test device 2 used in the animal test information according to the first embodiment of the present invention.

Figure 21:
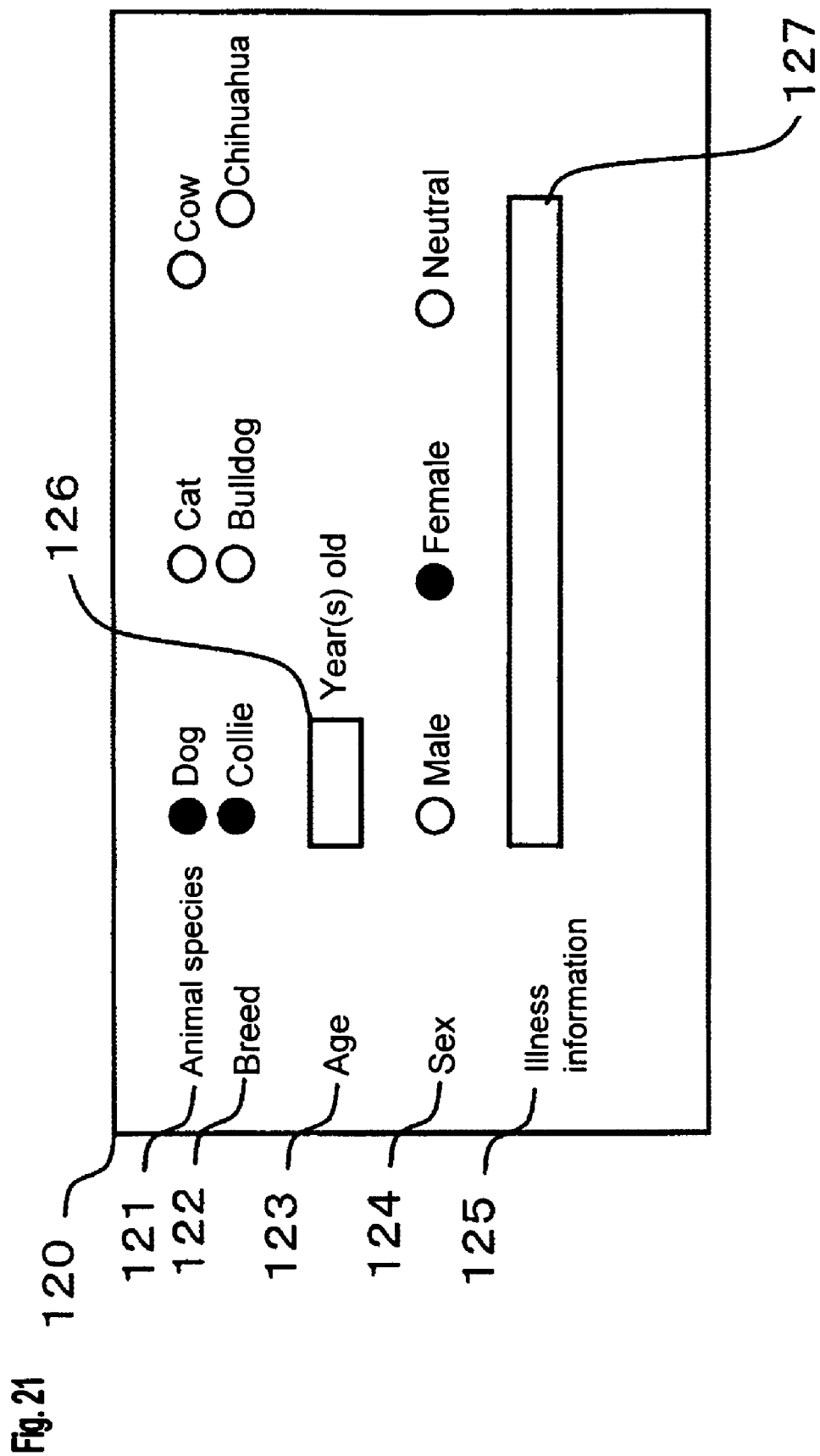
FIG. 21 is a view showing one example of an input screen of attribute information displayed on the calculation display device of the terminal test device used in the system for providing animal test information according to the first to the third embodiments of the present invention.

In FIG. 5, the CPU 21 of the calculation display device 2b of the terminal test device 2 receives attribute information of a sample to be measured via the input device 24 (step S501). The CPU 91 of the analyzer 2a may obviously directly receive the information via the display 19 and transmit the same to the calculation display device 2b. Here, the received attribute information is not limited to animal species (type of animals, dog, cat, . . . ), and information related to breed (intrinsic brand of animals: in the case of dogs, collie, bulldog, Chihuahua, . . . ), age, sex, type of affected illness and the like, but is not limited thereto. FIG. 21 shows one example of an input screen of the attribute information displayed on the input device 24 in step S501. As shown in the figure, the input screen 120 is displayed with an animal species selecting region 121, a breed selecting region 122, an age input region 123, a sex selecting region 124, and an illness information input region 125. In the animal species selecting region 121, one selection from dog, cat, and cow is received as animal species. In this figure, a state where the dog is selected is shown. The breed selecting region 122 is configured to display the breed corresponding to the animal species selected in the animal species selecting region 121. In the figure, since dog is selected as the animal species, collie, bulldog, and Chihuahua, which are breed corresponding to dog, are displayed. In this figure, a state where the collie is selected is shown. In the age input region 123, the age of an animal to be tested is input to an input field 126 by using the input device 24. In the sex selecting region 124, one selection of male, female, and neutral is received as sex. In this figure, a state where female is selected is shown. In the illness information input region 125, information related to the type of affected illness and the like is input to an input field 127 by using the input device 24.

The CPU 21 transmits instruction information to start the measurement of the sample to the analyzer 2a (step S502). The analyzer 2a executes an analyzing process of the sample, and the CPU 91 receives the property value information measured in the detector 17 and transmits the same to the calculation display device 2b. The CPU 21 of the calculation display device 2b judges whether or not the property value information is received from the analyzer 2a (step S503), and the process is in the standby state until being judged that the relevant information is received (step S503: NO). When the CPU 21 judges that the property value information is received (step S503: YES), the CPU 21 transmits the received property value information to the central device 3 in correspondence with the attribute information received in step S501 (step S504).

Figure 6:
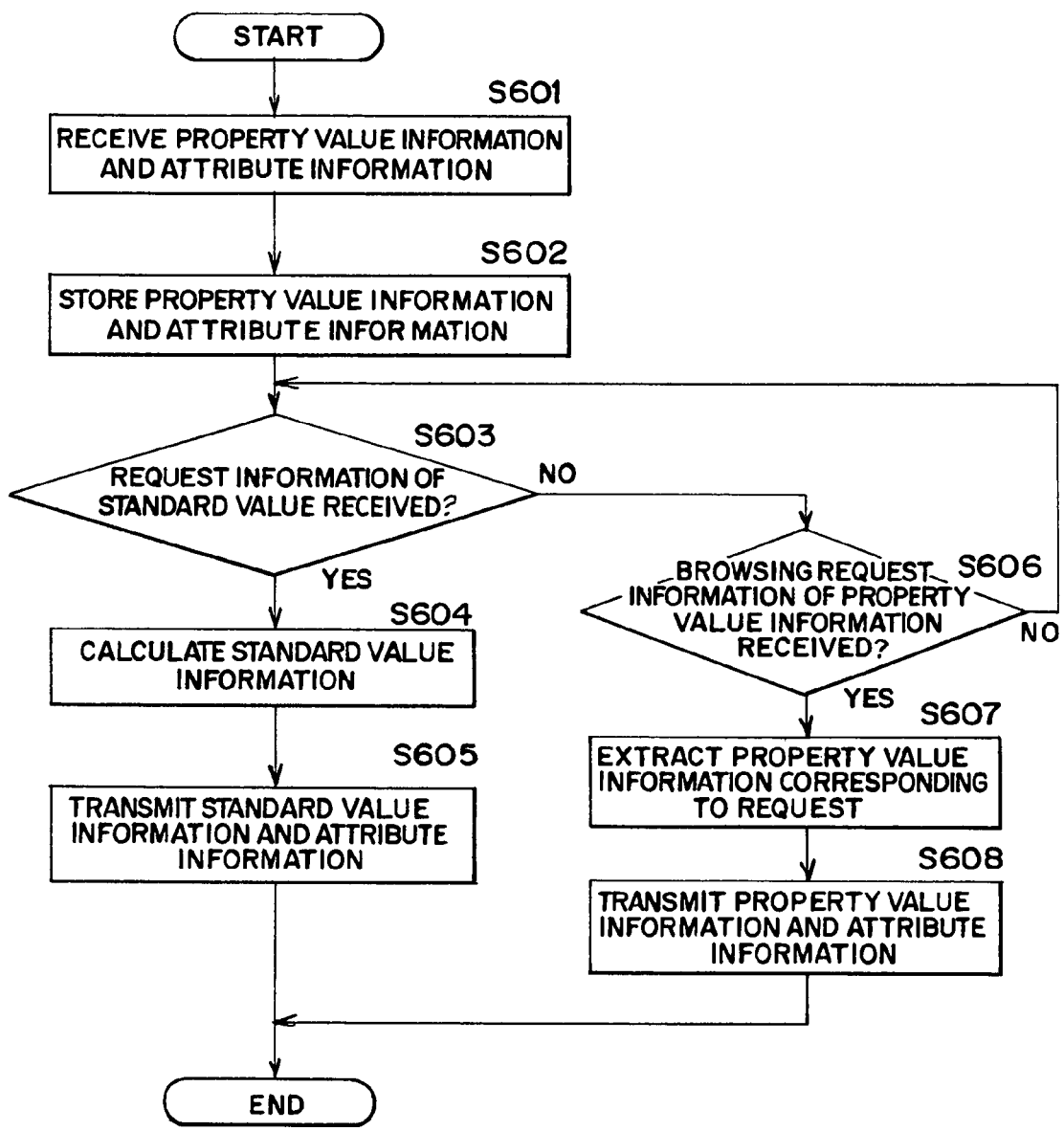
FIG. 6 is a flowchart showing a processing procedure of the CPU of the central device used in the system for providing animal test information according to the first embodiment of the present invention.

FIG. 6 is a flowchart showing a processing procedure of the CPU 31 of the central device 3 used in the system for providing animal test information according to the first embodiment of the present invention. In FIG. 6, the CPU 31 of the central device 3 receives the property value information corresponded with the attribute information (step S601), and stores the received property value information and the attribute information in the property value information storage 341 of the storage device 34 (step S602).

Figure 7:
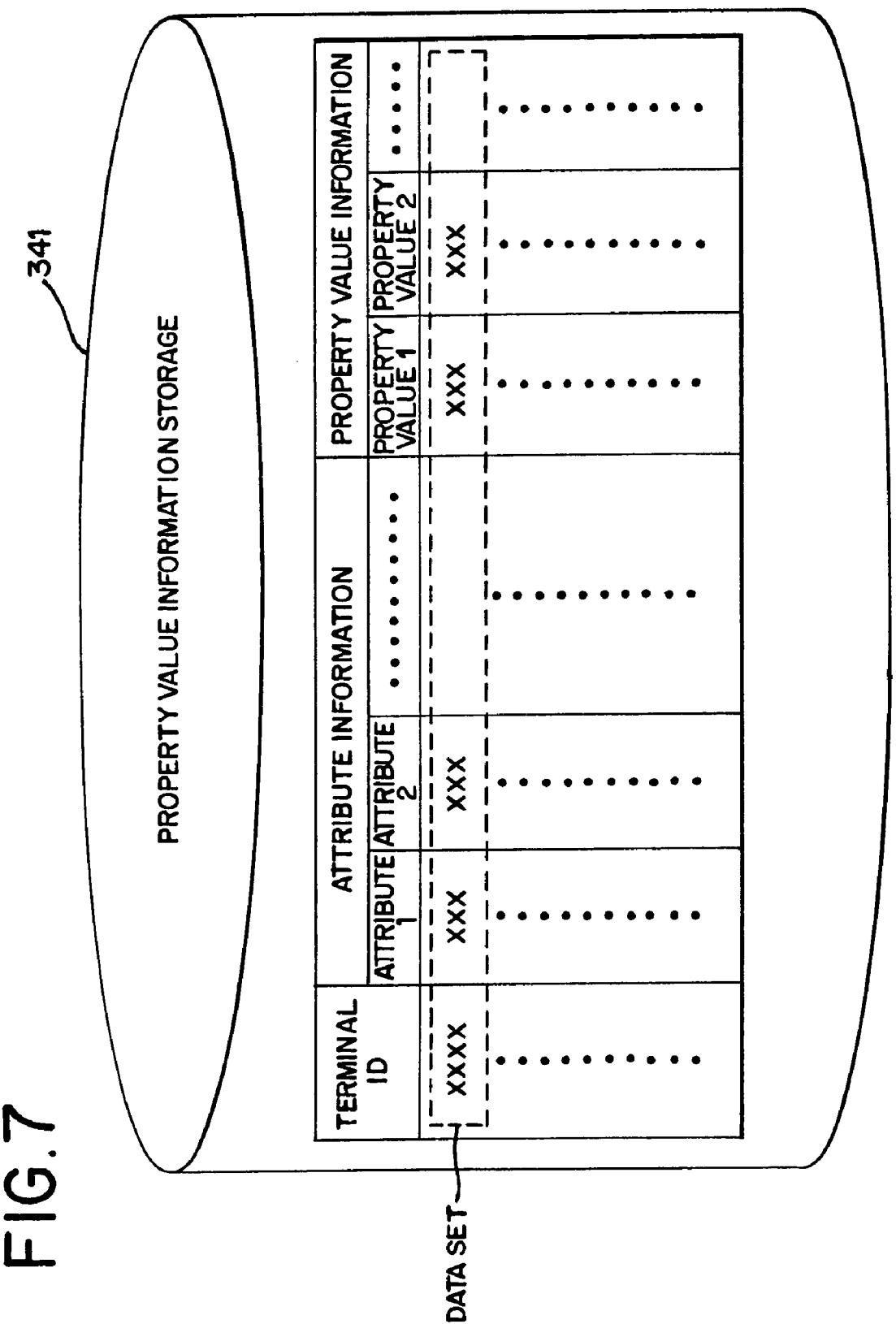
FIG. 7 is an illustrative view of a data structure stored in a property value information storage.

FIG. 7 is an illustrative view of a data structure stored in the property value information storage 341. As shown in FIG. 7, identification information capable of identifying the terminal test device 2 which is the transmission source, such as the attribute information and the property value information, are stored in correspondence with a terminal ID. The information is necessary to specify the terminal test device 2, serving as the transmission source, of the property value information serving as the basis of the standard value information calculation after calculating the standard value information used to determine the treatment of the animal based on the property value information. The attribute information is configured by a plurality of attribute 1, attribute 2, . . . , and the property value information is also configured by a plurality of property value 1, property value 2, . . . .

Returning to FIG. 5, the CPU 21 of the calculation display device 2b of the terminal test device 2 judges whether or not the request information of the information related to the result determination is received via the input device 24 (step S505). If the CPU 21 is not received the request information (step S505: NO), whether or not a browsing request of the property value information is received via the input device 24 is judged (step S509). If judged that the request information is received in step S505 (step S505: YES), the CPU 21 transmits the request information of the standard value to the central device 3 (step S506). If judged that the browsing request of the property value information is received in step S509 (step S509: YES), the browsing request information of the property value information is transmitted to the central device 3 (step S510). The browsing request of the property value information may include animal species or breed requesting to browse, may include data for identifying an animal (individual) to be tested (e.g., ID for identifying the animal), or may include a terminal ID for identifying the device which carried out the test. Furthermore, the browsing request of the property value information may include data indicating the period of requesting the browsing. If judged that the browsing request of the property value information is not received in step S509 (S509: NO), the process returns to step S505.

Returning to FIG. 6, the CPU 31 of the central device 3 judges whether or not the request information of the standard value is received (step S603), when the CPU 31 judges that the request information is received (step S603: YES), the CPU 31 calculates the standard value information used to determine the treatment of the animal based on the property value information for every attribute information based on the great amount of property value information collected in the property value information storage 341 (step S604). The standard value information calculated here is information related to the standard value used to determine the treatment of the animal based on the property value information, and is, for example, an average value calculated for every attribute information. Whether or not the received property value information is a normal value can be judged using the standard value information, for example, by defining predetermined upper and lower widths of a normal range for judging whether or not the property value information is normal (i.e., whether or not the tested animal is healthy). The standard value information may, of course, include a maximum value and a minimum value having the predetermined upper and lower widths of the normal range. In addition, when a constant amount of property value information can be collected, the range for judging that the property value information is normal may be specified by calculating a normal distribution of the measured property values and performing a statistical calculation based on the collected property value information.

Figure 8:
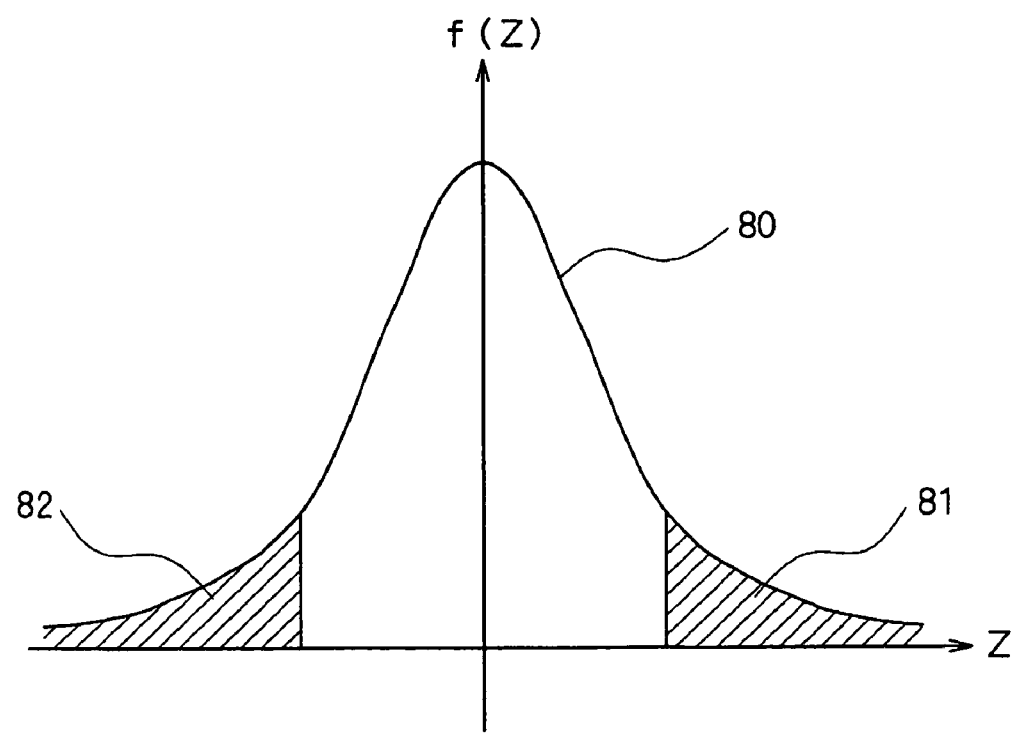
FIG. 8 is an illustrative view of a probability density function.

When using the normal distribution, for example, the CPU 31 judges whether or not the acquired predetermined property value $Z$ is on the maximum side or the minimum side of a probability density function $f(Z)$ or within a predetermined range of both. FIG. 8 is an illustrative view of the probability density function $f(Z)$. As shown in FIG. 8, the CPU 31 calculates an average value and a variance of the property value to calculate a probability density function 80. The probability density function $f(Z)$ may be obtained after excluding in advance the property values near the maximum value and near the minimum value in order to exclude abnormal values. The probability density function $f(Z)$ can be expressed as (equation 1). Here, $\sigma$ in (equation 1) is the standard deviation of the property value $Z$, and is calculated by (equation 2).

$$f(Z) = \frac{1}{\sqrt{2\pi}\cdot\sigma} e^{\frac{(Z-\bar{u})^2}{2\sigma^2}} \qquad \text{[Equation 1]}$$

wherein $\bar{u}$ is the average of the distribution.

$$\sigma = \sqrt{\sum_{i=1}^{n}(Zi-\bar{Z})^2} \qquad \text{[Equation 2]}$$

wherein $\bar{Z}$ is the average of the property value.

If judged that the property value is not included in the normal range, it can be considered as a case within a range corresponding to a few %, for example, 5 to 10% of the total in the region 81 on the maximum value side or the region 82 on the minimum value side of the probability density function 80. Therefore, when the acquired property value Z is included in the region 81 or 82, the property value Z can be judged as the property value that is not normal.

Therefore, in this case, as for the information the central device 3 transmits to the terminal test device 2 as standard value information, at least the probability density function f(Z) merely needs to be transmitted. It should be obviously recognized that a boundary value (percentage) indicating which range is judged as normal may be included. In addition, the information transmitted to the terminal test device 2 as the standard value information changes according to the statistical processing procedure.

Returning to FIG. 6, the CPU 31 of the central device 3 transmits the standard value information corresponding to the received attribute information as the information related to the result determination to the terminal test device 2, which is the transmission source of the property value information (step S605). For example, the standard value information corresponding to animal species of "dog", and the breed of "collie" is transmitted to the terminal test device 2 that has transmitted the property value information in animal species of "dog", and the breed of "collie". In this manner, even in a case where only the property value information insufficient to specify with the terminal test device 2 alone is provided, the standard value information of high reliability can be acquired, and the judgment of the doctors can be assisted. If the request information is not received in step S603 (step S603: NO), the CPU 31 of the central device 3 judges whether or not the browsing request of the property value information is received (step S606). If the browsing request of the property value information is received (YES in step S606), the property value information corresponding to the request is extracted from the property value information storage 341. For instance, if the animal species or the breed is included in the request information transmitted in step S510, the CPU 31 extracts all property value information corresponded with the relevant animal species or the breed from the property value information storage 341. If the ID for identifying the test target is included in the request information transmitted in step S510, all property value information of the animal specified by the ID are extracted from the property value information storage 341. The CPU 31 transmits the extracted property value information along with the data such as the animal species contained in the request information to the terminal test device 2 in step S608.

Returning back to FIG. 5, the CPU 21 of the calculation display device 2b of the terminal test device 2 receives the standard value information related to the attribute information corresponding to the property value information transmitted to the central device 3 as information related to the result determination (step S507), and displays the information related to the result determination on the display device 25 with the standard value information (step S508). The format of displaying on the display device 25 is not particularly limited, but the comparison between the standard value information and the measured property value information is desirably visually made.

Figure 9:
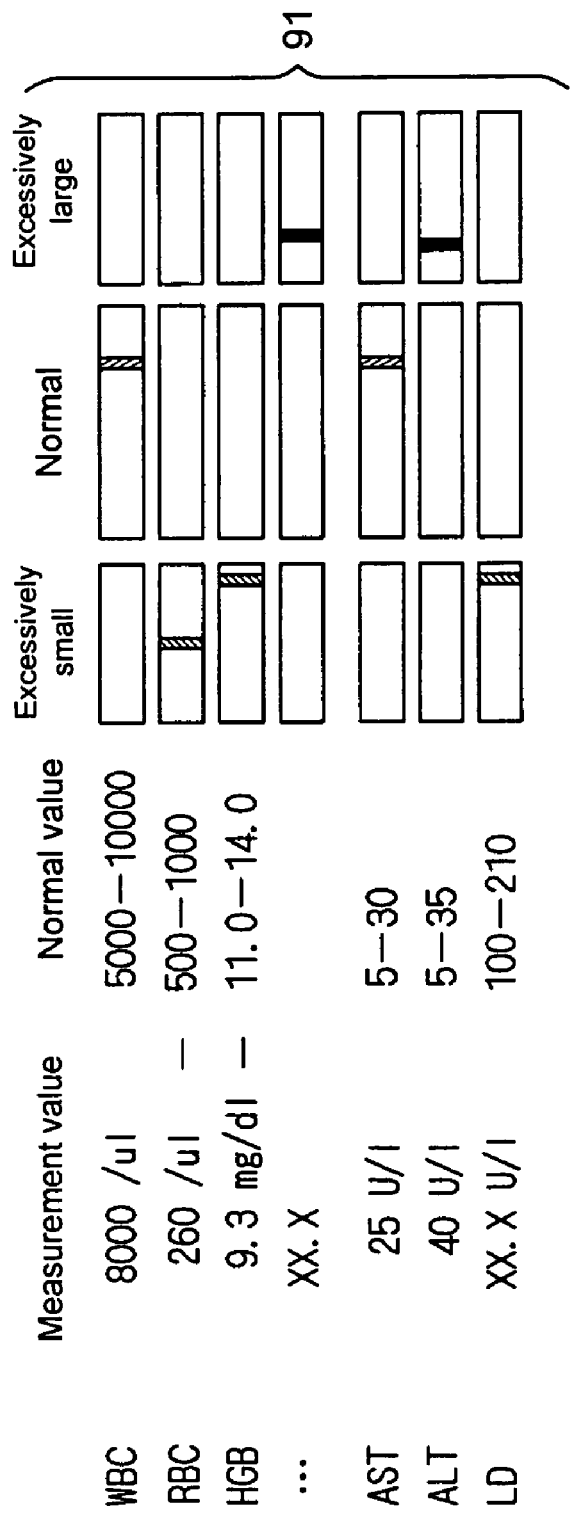
FIG. 9 is an illustrative view of a screen displayed on a display device as information related to a result determination.

FIG. 9 is an illustrative view of a screen displayed on the display device 25 as information related to the result determination. In FIG. 9, the measurement value of each item serving as the property value information, and the normal range of each displayed item serving as the standard value information are respectively displayed. Such information are displayed using a slide bar 91 such that whether the actually measured property value information is "excessively small", "normal", or "excessively large" with respect to the normal range can be visually checked. Whether or not the measured property value information is normal can be then visually checked.

Figure 10:
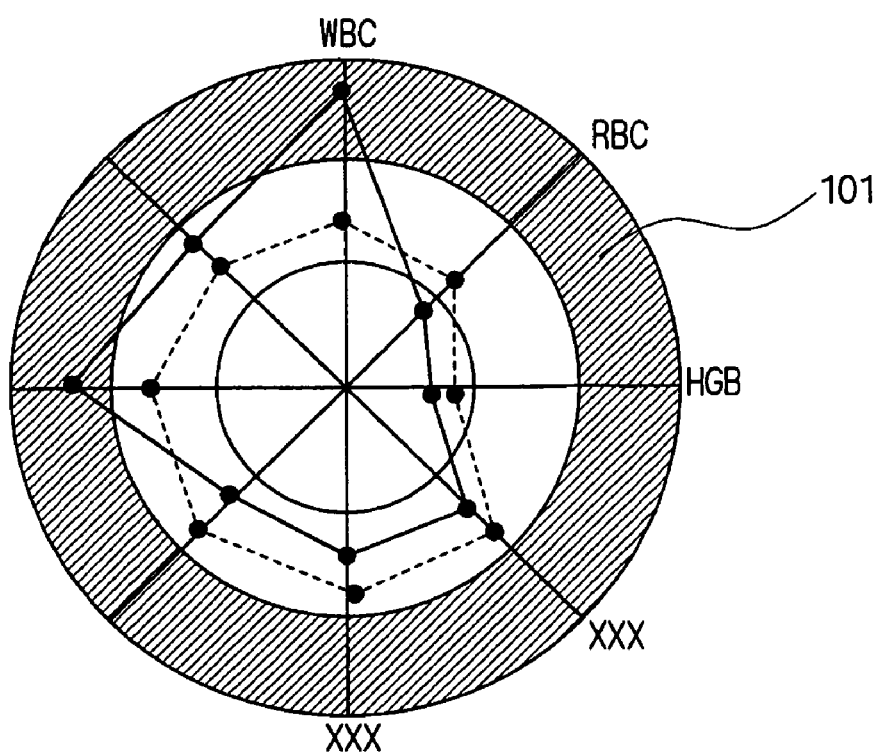
FIG. 10 is another illustrative view of a screen displayed on the display device as information related to a result determination.

FIG. 10 is another illustrative example of a screen displayed on the display device 25 as information related to the result determination. In FIG. 10, the measurement value of each item serving as the property value information is sampled, and the relationship with the normal range of each item displayed as the standard value information is displayed as a radar chart. In a hatching part 101, the outer circumferential portion shows the maximum value of the normal range, and the internal circumferential portion shows the minimum value of the normal range, whether or not the property value information measured for every item is in the normal range can be visually checked depending on whether or not the measured property value information is contained in the hatching part 101.

Figure 11:
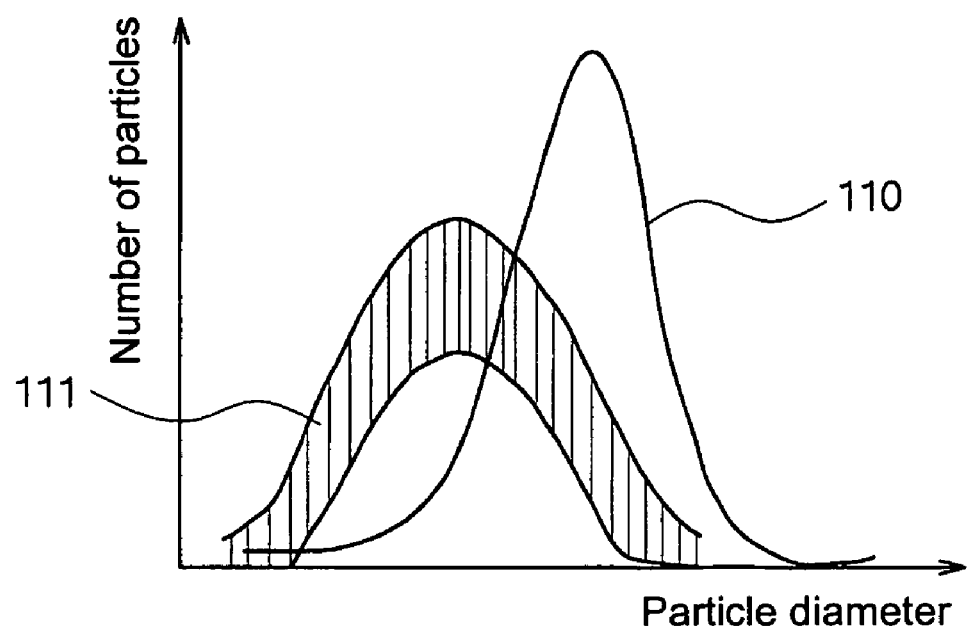
FIG. 11 is an illustrative view of a screen displayed on the display device 25 of the case of comparing the distribution state of the property value information.

Depending on the property value information, the normal range may not be simply defined. In this case, whether normal or not needs to be sensuously judged by comparing with the distribution of a normal case. FIG. 11 is an illustrative view of a screen displayed on the display device 25 of the case of comparing the distribution state of the property value information.

In FIG. 11, a distribution range where a hatching part 111 is judged as normal with respect to the measurement value 110 showing the relationship between the number of particles and the particle diameter of the measured red blood cells is shown. In the example of FIG. 11, the particle diameter at the maximum value of the measurement value 110 is larger than the particle diameter at the maximum value of the hatching part 111, and thus judgment can be made that the number of red blood cells having a large particle diameter is contained in excess than the normal range in the measured blood. If judged that the browsing request is received in step S509 (step S509: YES), and the request information is transmitted to the central device 3, the information transmitted from the central device 3 in step S608 is received (step S511), and displayed (step S512). FIG. 19 is a view showing one example of a screen displayed in step S512. This example shows a case where "dog" is included as the animal species and Oct. 1, 2007 to Nov. 30, 2007 are included as the period in the request information transmitted in step S510, and all property value information from Oct. 1, 2007 to Nov. 30, 2007 with respect to the animal species "dog" are displayed. If "collie" is included as the animal species in the request information transmitted in step S510, the breed "collie" is displayed instead of the animal species "dog" on the screen of FIG. 19, and all property value information from Oct. 1, 2007 to Nov. 30, 2007 with respect to the breed "collie" are displayed. The reception of the request information in steps S505 and 509, and the display of the screen shown in FIG. 19 in step S508 can be executed through the Internet browser.

Therefore, according to the first embodiment, the property value information of the animal having the attribute information where the absolute number is insufficient with each terminal test device can be collected by a constant amount by aggregating the property value information from the plurality of terminal test devices, and the standard value information based on greater property value information can be calculated by calculating the standard value information used to determine the treatment of the animal based on the collected property value information. Therefore, even in animals having attribute information in which sufficient test data are not held in one veterinary hospital or unknown attribute information, the doctor can determine the treatment of the animals based on a more objective standard value information without depending on intuition and experience. Since the central device 3 receives, stores, and outputs the property value information transmitted from a plurality of terminal test devices 2 in correspondence to the attribute information indicating the type or the breed of the animal, and thus reference of great number of property value information on a specific animal species or breed is facilitated.

The standard value information can be updated in the central device 3 at substantially real time according to the collected property value information. Therefore, when receiving the property value information serving as the measurement result of an animal sample rare in our country and having the attribute information such as animal species, the treatment of the animal can be determined using the standard value information updated using the most recent property value information, and an accurate diagnosis can be assisted with respect to an event where judgment is difficult in the veterinary clinic alone. In the first embodiment, the reception of the request information in steps S505 and 509 and the display of the screen shown in FIG. 19 in step S508 are executed in the terminal test device 2, but such operations may be executed using the Internet browser installed in a computer other than the terminal test device 2 and the central device 3.

Second Embodiment

A system for providing animal test information according to a second embodiment of the present invention will be specifically described below based on the drawings. The configuration of the system for providing animal test information according to the second embodiment of the present invention is similar to the first embodiment, but differs from the first embodiment in that the standard value information taking correction into consideration is calculated in the central device 3 in view of the fact that the property value information respectively measured in the terminal test device 2, 2, . . . is corrected. The basic configurations of the central device 3 and the terminal test device 2 are similar to the first embodiment, and thus detailed description will be omitted by denoting the same reference numerals.

Figure 12:
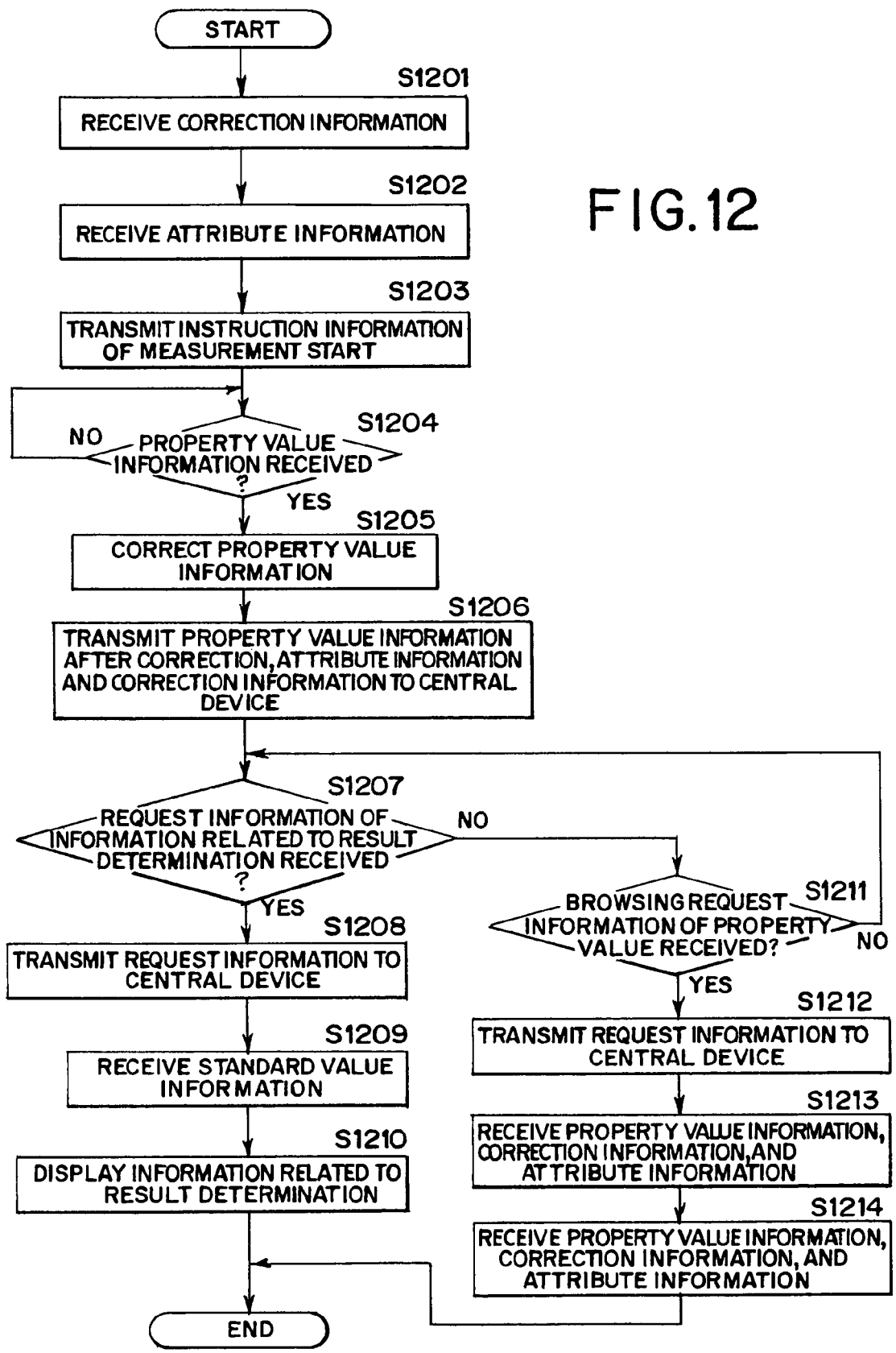
FIG. 12 is a flowchart showing a processing procedure of the CPU of the terminal test device used in a system for providing animal test information according to a second embodiment of the present invention.

The processing procedure in the terminal test device 2 and the central device 3 in the system for providing animal test information according to the second embodiment will be described. FIG. 12 is a flowchart showing a processing procedure of the CPU 21 of the terminal test device 2 used in the system for providing animal test information according to the second embodiment of the present invention.

In FIG. 12, the CPU 21 of the calculation display device 2b of the terminal test device 2 receives correction information input or set through the display 19 of the analyzer 2a (step S1201). Obviously, the CPU 21 of the calculation display device 2b may receive the correction information via the input device 24, or may receive the correction information set in time of delivery and stored in the RAM 92 of the control substrate section 9 of the analyzer 2a via the communication interface 95.

Here, the correction information means a correction coefficient of correcting the property value information measured in the analyzer 2a so as to become the measurement value with the measurement value measured in another measurement device as a true value. For instance, if the measured property value information is the hematocrit value HCT, the measurement value HCT1 in the analyzer 2a and the measurement value HCT2 in the measurement device using a centrifugal hematocrit method often installed in veterinary hospitals differ in the measurement value. In this case, assuming that the measurement value HCT2 in the centrifugal hematocrit method is the correct value, correction is made by multiplying the correction coefficient α so that the measurement value HCT1 in the analyzer 2a becomes the measurement value HCT2. In this case, the correction coefficient α is obtained as in (equation 3).

$$\alpha = HCT2/HCT1 \qquad \text{(Equation 3)}$$

The correction coefficient related to other property value information is also similarly calculated if necessary. Therefore, the standard value information used to determine the treatment of the animal can be more accurately calculated based on the original property value information before correction by transmitting not only the property value information but also the correction coefficient for every property value information to the central device 3. Therefore, the treatment of the animal can be determined using the standard value information updated using the most recent property value information.

The CPU 21 of the calculation display device 2b of the terminal test device 2 then receives the attribute information of the sample to be measured via the input device 24 (step S1202). The CPU 91 of the analyzer 2a may, of course, directly receive the information through the display 19, and transmit the same to the calculation display device 2b. The attribute information to receive is not limited to animal species (type of animal: dog, cat, . . . ), and information related to breed (intrinsic brand of animals: in the case of dogs, collie, bulldog, Chihuahua, . . . ), age, sex, and the like, but is not limited thereto.

The CPU 21 transmits instruction information to start the measurement of the sample to the analyzer 2a (step S1203). The analyzer 2a executes an analyzing process of the sample, and the CPU 91 receives the property value information measured in the detector 17 and transmits the same to the calculation display device 2b in correspondence with the received attribute information. The CPU 21 of the calculation display device 2b judges whether or not the property value information is received from the analyzer 2a (step S1204), and the process is in the standby state until being judged that the relevant information is received (step S1204: NO). When the CPU 21 judges that the property value information is received (step S1204: YES), the CPU 21 corrects the property value information based on the received property value information and the correction information (step S1205), and transmits the corrected property value information, the attribute information, and the correction information to the central device 3 (step S1206).

Figure 13:
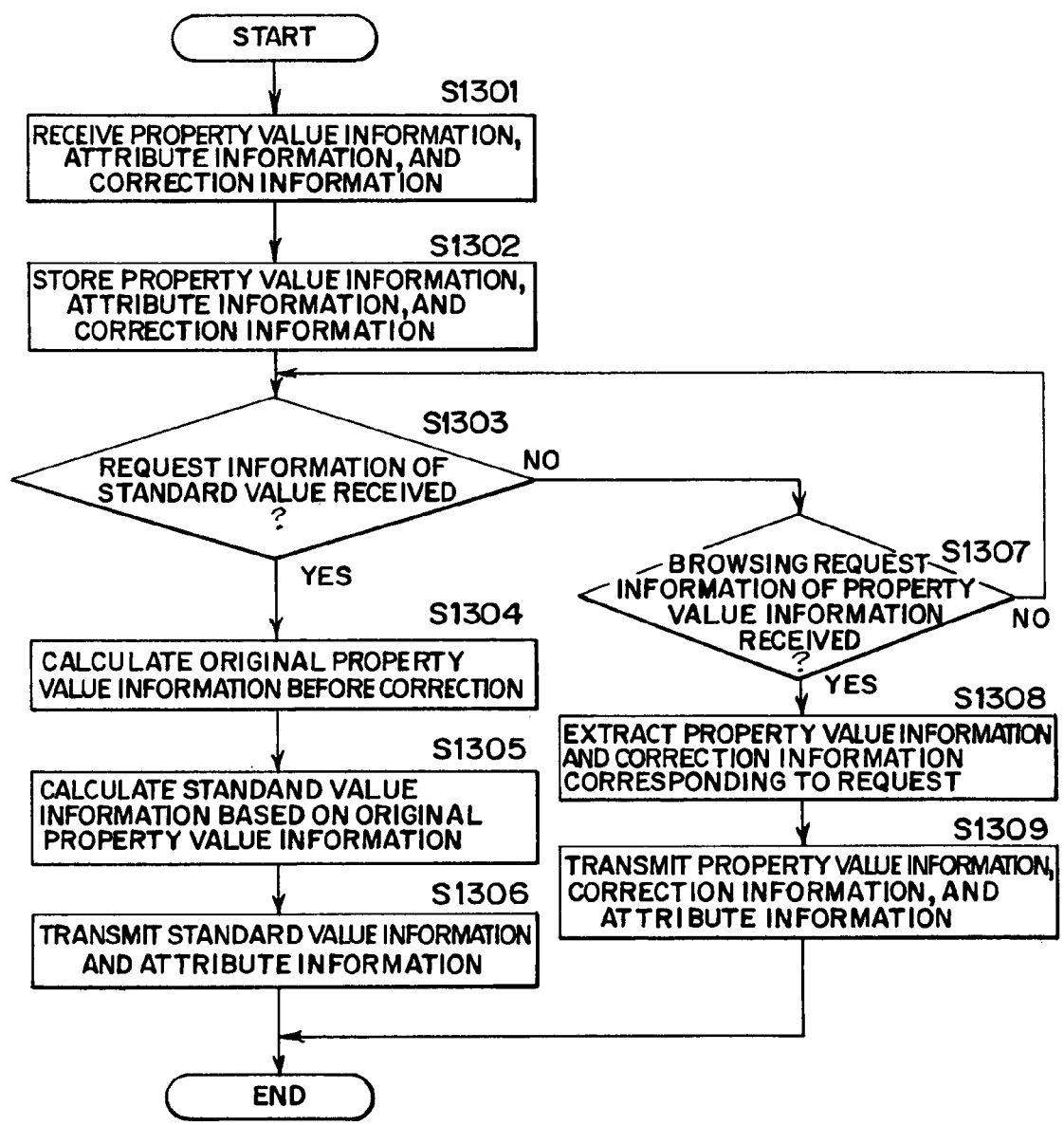
FIG. 13 is a flowchart showing a processing procedure of the CPU of the central device used in the system for providing animal test information according to the second embodiment of the present invention.

FIG. 13 is a flowchart showing a processing procedure of the CPU 31 of the central device 3 used in the system for providing animal test information according to the second embodiment of the present invention. In FIG. 13, the CPU 31 of the central device 3 receives the property value information corresponded with the attribute information, the attribute information, and the correction information (step S1301), and stores the received property value information, attribute information and correction information in the property value information storage 341 of the storage device 34 (step S1302).

Figure 14:
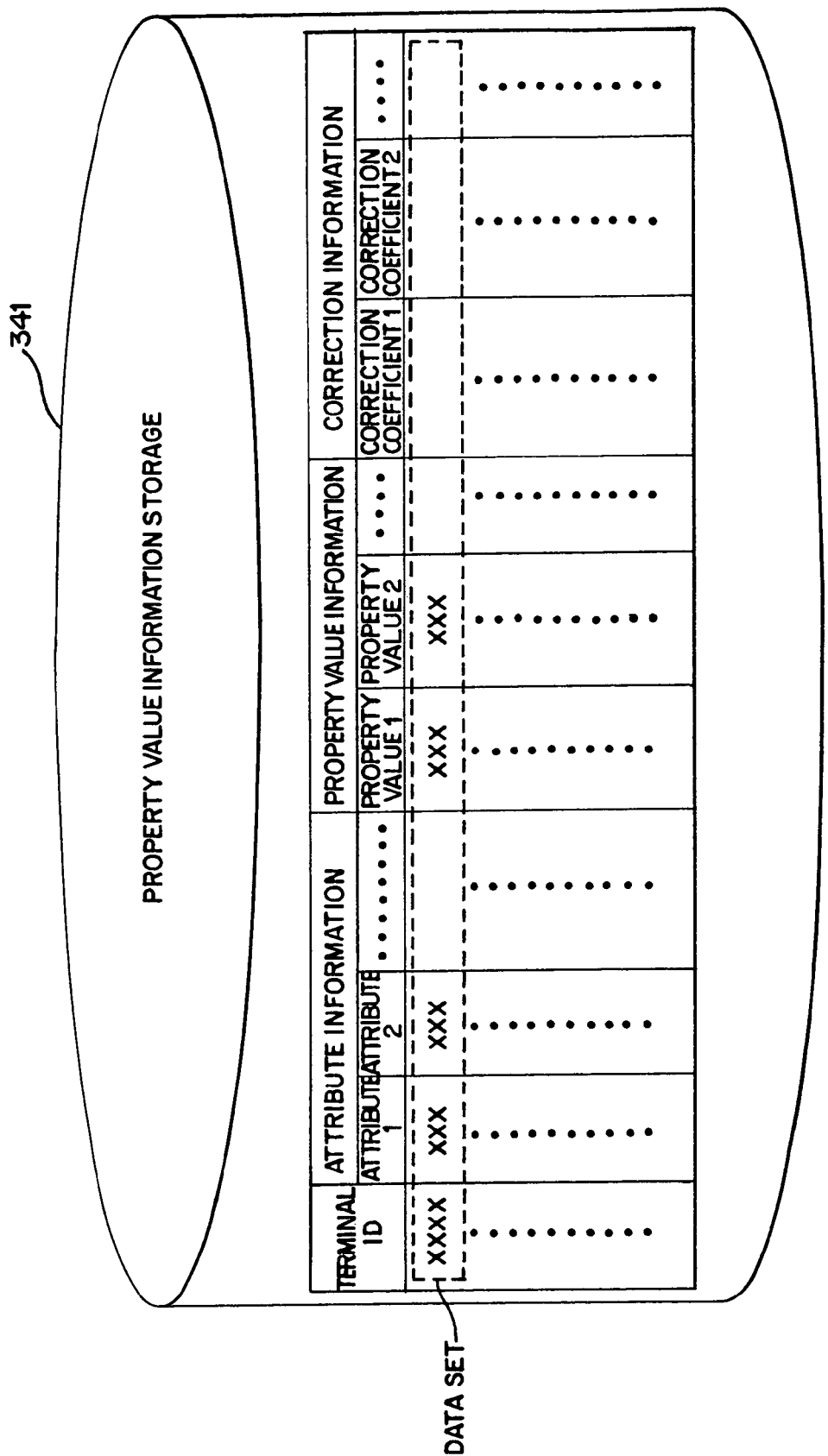
FIG. 14 is an illustrative view of a data structure stored in a property value information storage.

FIG. 14 is an illustrative view of a data structure stored in the property value information storage 341. As shown in FIG. 14, identification information capable of identifying the terminal test device 2, which is the transmission source, such as the attribute information, the property value information and the correction information for every property value information are stored in correspondence with a terminal ID. The attribute information is configured by a plurality of attribute 1, attribute 2, . . . , and the property value information is also configured by a plurality of property value 1, property value 2, . . . . The correction information is stored by the number of property value information where the correction information corresponding to the property value 1 is correction coefficient 1, the correction information corresponding to the property value 2 is correction coefficient 2, and so on.

Returning to FIG. 12, the CPU 21 of the calculation display device 2b of the terminal test device 2 judges whether or not the request information of the information related to the result determination is received via the input device 24 (step S1207). If the CPU 21 has not received the request information (step S1207: NO), whether or not a browsing request of the property value information is received via the input device 24 is judged (step S1211). If judged that the request information is received in step S1207 (step S1207: YES), the CPU 21 transmits the request information to the central device 3 (step S1208). If judged that the browsing request of the property value information is received in step S1211 (step S1211: YES), the browsing request information of the property value information is transmitted to the central device 3 (step S1212). The browsing request of the property value information may include animal species or breed requesting to browse, may include data for identifying an animal (individual) to be tested (e.g., ID for identifying the animal), or may include a terminal ID for identifying the device which carried out the test. Furthermore, the browsing request of the property value information may include data indicating the period of requesting the browsing. If judged that the browsing request of the property value information is not received in step S1211 (S1211: NO), the process returns to step S1207.

Returning to FIG. 13, the CPU 31 of the central device 3 judges whether or not the request information is received (step S1303), when the CPU 31 judges that the request information is received (step S1303: YES), the CPU 31 calculates the original standard value information serving as the property value information before correction based on the stored property value information and the correction information (step S1304), and calculates the standard value information of the property value for every attribute information based on the great amount of original property value information collected in the property value information storage 341 (step S1305).

The standard value information calculated here is information related to the standard value used to determine the treatment of the animal based on the property value information, similar to the first embodiment, and is, for example, an average value calculated for every attribute information. Whether or not the received property value information is a normal value can be judged using the standard value information, for example, by defining predetermined upper and lower widths of a normal range for judging whether or not the property value information is normal. The standard value information may, of course, include a maximum value and a minimum value having the predetermined upper and lower widths of the normal range. In addition, when a constant amount of property value information can be collected, the range for judging that the property value information is normal may be specified by calculating a normal distribution of the measured property values and performing a statistical calculation based on the collected property value information.

The CPU 31 transmits the standard value information corresponding to the received attribute information to the terminal test device 2, which is the transmission source of the property value information (step S1306). For example, the standard value information corresponding to animal species of "dog", and the breed of "collie" is transmitted to the terminal test device 2 that has transmitted the property value information in animal species of "dog", and the breed of "collie". In this manner, even in a case where only the property value information insufficient to specify with the terminal test device 2 alone is provided, the standard value information of high reliability can be acquired, and the judgment of the doctors can be assisted. Since the standard value information is calculated based on the original property value information before correction, the precision of the standard value information becomes higher, and the judgment precision on whether or not the measured property value information is normal becomes higher. If the request information is not received in step S1303 (step S1303: NO), the CPU 31 of the central device 3 judges whether or not the browsing request of the property value information is received (step S1307). If the browsing request of the property value information is received (YES in step S1307), the property value information corresponding to the request and the correction information are extracted from the property value information storage 341. For instance, if the animal species or the breed is included in the request information transmitted in step S1212, the CPU 31 extracts all of the property value information and the correction information corresponded with the relevant animal species or the breed from the property value information storage 341. If the ID for identifying the test target is included in the request information transmitted in step S1212, all of the property value information and the correction information of the animal specified by the ID are extracted from the property value information storage 341. The CPU 31 transmits the extracted property value information along with the data such as the animal species contained in the request information to the terminal test device 2 in step S1309.

Returning back to FIG. 12, the CPU 21 of the calculation display device 2b of the terminal test device 2 receives the standard value information related to the attribute information corresponding to the property value information transmitted to the central device 3 (step S1209), and displays the information related to the result determination on the display device 25 with the standard value information (step S1210). The format of displaying on the display device 25 is not particularly limited, and various display formats may be used, similar to the first embodiment. If judged that the browsing request is received in step S1211 (step S1211: YES), and the request information is transmitted to the central device 3, the information transmitted from the central device 3 in step S1309 is received (step S1213), and displayed (step S1214). FIG. 20 is a view showing one example of a screen displayed in step S1214. This example shows a case where "dog" is included as the animal species and Oct. 1, 2007 to Nov. 30, 2007 is included as the period in the request information transmitted in step S1212, and all property value information from Oct. 1, 2007 to Nov. 30, 2007 with respect to the animal species "dog" are displayed. The correction information is also displayed on the screen in correspondence with the respective property value information. The correction information is displayed as "1" if the correction is not performed. If "collie" is included as the animal species in the request information transmitted in step S1212, the breed "collie" is displayed instead of the animal species "dog" on the screen of FIG. 20, and the property value information from Oct. 1, 2007 to Nov. 30, 2007 with respect to the breed "collie" are displayed with the correction information. The reception of the request information in steps S1207 and 1211, and the display of the screen shown in FIG. 20 in step S1214 can be executed through the Internet browser.

The standard value information calculated based on the original property value information before correction is not limited to being transmitted to the terminal test device 2, and the calculated standard value information may be corrected in the central device 3, and then the corrected standard value information may be transmitted to the terminal test device 2. FIG. 15 is a flowchart showing another processing procedure of the CPU 31 of the central device 3 used in the system for providing animal test information according to the second embodiment of the present invention.

In FIG. 15, the processes up to step S1305 are similar to FIG. 13, and thus the detailed description will be omitted. The CPU 31 of the central device 3 corrects the calculated standard value information based on the stored correction information (step S1501), and transmits the corrected standard value information corresponding to the received attribute information to the terminal test device 2, which is the transmission source of the property value information (step S1502).

In this manner, whether or not the measured property value information is included in the normal range, and the like, can be checked and the treatment of the animal can be determined by using the received standard value information as is without correcting in the terminal test device 2 receiving the standard value information.

Therefore, according to the second embodiment, the variation in the measured property value information by the correction information set at different values for every terminal test device 2 can be corrected, and the standard value information of higher precision can be calculated. In the second embodiment, the CPU 91 transmits the corrected property value information in step S1206, but the property value information before correction may be transmitted to the central device 3 along with the attribute information and the correction information.

Third Embodiment

A system for providing animal test information according to a third embodiment of the present invention will be specifically described based on the drawings. FIG. 16 is a block diagram showing a configuration of a system for providing animal test information according to the third embodiment of the present invention. The configuration of the system for providing animal test information according to the third embodiment is substantially the same as the first embodiment, but differs from the first embodiment in that an illness information storage 342 and/or treatment information storage 343 are arranged in the storage device 34 of the central device 3. The basic configurations of the central device 3 and the terminal test device 2 are similar to the first embodiment, and thus the detailed description will be omitted by denoting the same reference numerals.

The illness information storage 342 arranged in the storage device 34 of the central device 3 stores illness information related to the corresponding illness based on the illness judgment condition information including the relationship and the like that the measured property value information needs to have with the standard value information in correspondence with the attribute information. The illness information is preferably stored as a message to be displayed on the display device 25 of the terminal test device 2. This is because the doctors can visually acquire the information.

For instance, with the HGB (hemoglobin content) smaller than the normal range and the MCV (mean corpuscular volume) smaller than the normal range as the illness judgment condition information, text data "possible microcytic hypochromic anemia, iron-deficiency anemia and the like" is stored as a corresponding message. With the HGB (hemoglobin content) and the MCV (mean corpuscular volume) in the normal range, the RBC smaller than the normal range, and the LDH smaller than the normal range as the illness judgment condition information, text data "possible macrocytic anemia, anaplastic anemia, hemolytic anemia, megaloblastic anemia, liver disorder and the like" is stored as a corresponding message. The possibility of illness can be determined in the central device 3 and transmitted to the terminal test device 2 by storing the illness information (message) in correspondence to the illness judgment condition information for judging the various illnesses.

FIG. 17 is a flowchart showing a processing procedure of the CPU 31 of the central device 3 used in the system for providing animal test information according to the third embodiment of the present invention. In FIG. 17, the CPU 31 of the central device 3 receives the property value information corresponded with the attribute information (step S1701), and stores the received property value information and the attribute information in the property value information storage 341 of the storage device 34 (step S1702).

The CPU 31 judges whether or not the request information is received from the terminal test device 2 (step S1703), and the process is in the standby state until the CPU 31 judges that the request information is received (step S1703: NO). When the CPU 31 judges that the request information is received (step S1703: YES), the CPU 31 calculates the standard value information of the property value information for every attribute information based on the great amount of property value information collected in the property value information storage 341 (step S1704).

Similar to the first and the second embodiments, the standard value information calculated here is the information related to the standard value used to determine the treatment of the animal based on the property value information, and is an average value calculated for every attribute information. Whether or not the received property value information is a normal value can be judged using the standard value information, for example, by defining predetermined upper and lower widths of a normal range for judging whether or not the property value information is normal. The standard value information may, of course, include a maximum value and a minimum value having the predetermined upper and lower widths of the normal range. In addition, when a constant amount of property value information can be collected, the range for judging that the property value information is normal may be specified by calculating a normal distribution of the measured property values and performing a statistical calculation based on the collected property value information.

The CPU 31 selects one property value information (step S1705), and judges whether or not the selected property value information is included in the specified normal range (step S1706). The CPU 31 stores as information related to the relative relationship between the property value information and the standard value information in the RAM 33 (step S1707) if the CPU 31 judges that the selected property value information is not included in the normal range (step S1706: NO), and the CPU 31 skips step S1707 and judges whether or not all property value information are selected (step S1708) if the CPU 31 judges that the selected property value information is included in the normal range (step S1706: YES). The information related to the relative relationship between the property value information and the standard value information is information related to the relative relationship such as the property value information A is smaller than the standard value information B, the property value information C is smaller than the standard value information D, and the like.

If the CPU 31 judges that the property value information which has not yet selected exists (step S1708: NO), the CPU 31 selects the next property value information (step S1709), returns the process to step S1706, and repeats the above-described processes. If the CPU 31 judges that all property value information are selected (step S1708: YES), the CPU 31 specifies the illness judgment condition information for referencing the illness information storage 342 based on the information related to the relative relationship between the property value information and the standard value information stored in the RAM 33 (step S1710).

The CPU 31 references the illness information storage 342 and judges whether or not the illness judgment condition information match (step S1711), and the CPU 31 extracts (step S1712) the illness information stored in the illness information storage 342 in correspondence to the illness judgment condition information when judged that the illness judgment condition information match (step S1711: YES).

The CPU 31 transmits the extracted illness information, the property value information, and the attribute information to the terminal test device 2, which is the transmission source of the property value information (step S1713). Thus, whether or not the property value information received in the central device 3 is included in the normal range is judged, and the illness information related to the assumed illness can be acquired in the terminal test device 2 based on the information related to the relative relationship between the property value information and the standard value information, and thus provision of a more accurate judgment to the owner of the animal can be assisted.

Not limited to the illness information, treatment information related to the treatment such as what kind of test may be added can also be transmitted to the terminal test device 2 through similar process. In this case, the treatment information storage 343 arranged in the storage device 34 of the central device 3 stores the treatment information related to the corresponding illness based on the treatment judgment condition information including the relationship and the like that the measured property value information needs to have with the standard value information in correspondence with the attribute information. The treatment information is preferably stored as a message to be displayed on the display device 25 of the terminal test device 2. This is because the doctors can visually acquire the information.

For instance, with the HGB (hemoglobin content) smaller than the normal range and the MCV (mean corpuscular volume) smaller than the normal range as the combining condition, text data "measurement of serum iron and TIBC is recommended. Possible iron-deficiency anemia if serum iron is small and the TIBC is normal or large" is stored as a corresponding message. Thus, not limited to the illness information, by storing the treatment information related to the treatment further necessary for checking, the treatment information necessary in the central device 3 is extracted and may be transmitted to the terminal test device 2 as a message.

FIG. 18 is a flowchart showing another processing procedure of the CPU 31 of the central device 3 used in the system for providing animal test information according to the third embodiment of the present invention. In FIG. 18, the CPU 31 of the central device 3 receives the property value information corresponded with the attribute information (step S1801), and stores the received property value information and the attribute information in the property value information storage 341 of the storage device 34 (step S1802).

The CPU 31 judges whether or not the request information is received from the terminal test device 2 (step S1803), and the process is in the standby state until the CPU 31 judges that the request information is received (step S1803: NO). When the CPU 31 judges that the request information is received (step S1803: YES), the CPU 31 calculates the standard value information of the property value information for every attribute information based on the great amount of property value information collected in the property value information storage 341 (step S1804).

The CPU 31 selects one property value information (step S1805), and judges whether or not the selected property value information is included in the specified normal range (step S1806). The CPU 31 stores as information related to the relative relationship between the property value information and the standard value information in the RAM 33 (step S1807) if the CPU 31 judges that the selected property value information is not included in the normal range (step S1806: NO), and the CPU 31 skips step S1807 and judges whether or not all property value information are selected (step S1808) if the CPU 31 judges that the selected property value information is included in the normal range (step S1806: YES). The information related to the relative relationship between the property value information and the standard value information is information related to the relative relationship such as the property value information A is smaller than the standard value information B, the property value information C is smaller than the standard value information D, and the like.

If the CPU 31 judges that the property value information has not yet selected exists (step S1808: NO), the CPU 31 selects the next property value information (step S1809), returns the process to step S1806, and repeats the above-described processes. If the CPU 31 judges that all property value information are selected (step S1808: YES), the CPU 31 specifies the treatment judgment condition information for referencing the treatment information storage 343 based on the information related to the relative relationship between the property value information and the standard value information stored in the RAM 33 (step S1810).

The CPU 31 references the treatment information storage 342 and judges whether or not the treatment judgment condition information match (step S1811), and the CPU 31 extracts (step S1812) the treatment information stored in the treatment information storage 343 in correspondence to the treatment judgment condition information when judged that the treatment judgment condition information match (step S1811: YES).

The CPU 31 transmits the extracted treatment information, the property value information, and the attribute information to the terminal test device 2, which is the transmission source of the property value information (step S1813). Thus, whether or not the property value information received in the central device 3 is included in the normal range is judged, and the treatment information related to the treatment to be conducted can be acquired in the terminal test device 2 based on the information related to the relative relationship between the property value information and the standard value information, and thus provision of a more accurate judgment to the owner of the animal can be assisted.

According to the configuration of each embodiment, the property value information of an animal having attribute information, in which absolute number is not sufficient in each terminal test device, can be collected by a constant amount by aggregating the property value information from the plurality of terminal test devices, and the standard value information based on greater amount of property value information can be calculated by calculating the standard value information used to determine the treatment of the animal based on the collected property value information. Therefore, even in animals having attribute information in which sufficient test data are not held in one veterinary hospital, or unknown attribute information, the doctor can determine the treatment of the animals based on a more objective standard value information without depending on intuition and experience.

According to the configuration of each embodiment, the test result of other samples of the animal species (or breed) same as the animal species (or breed) of the sample to be tested can be easily referenced by receiving, storing, and outputting the property value information from the plurality of animal terminal test devices in correspondence to the attribute information indicating the type or the breed of the animal.

The first to the third embodiments merely illustrate examples, and various modifications, replacements and the like can be carried out within a scope not deviating from the concept of the invention. Not limited to a mode of being configured by the analyzer 2a and the calculation display device 2b and having the analyzer 2a and the calculation display device 2b connected so as to be able to transmit and receive data, as described above, and the device may be an integrated mode. It should be recognized that the analyzer 2a of the terminal test device 2 can be easily applied to various analyzers capable of measuring and analyzing measurement values, such as blood cell counting device, biochemical analyzer, urine analyzer, immune analyzer, and the like.

Not limited to being connected with a single analyzer, a biochemical analyzer for conducting a biochemical test may be connected as the analyzer in addition to the blood cell counting device. Similar to the blood cell counting device, the biochemical analyzer receives the input of the attribute information, and transmits the received attribute information to the central device 3 in correspondence with the property value information. Here, the property value information is biochemical items including HDL and LDL.

If the biochemical analyzer is connected, more detailed information can be provided as the illness information. For instance, with TP (amount of total protein) small, Alb (amount of albumin) small, and Glob (amount of total globulin) normal as the combining condition, text data "Possible liver failure, glomus illness and the like" is stored as the corresponding message. With TP (amount of total protein) small, Alb (amount of albumin) small, and Glob (amount of total globulin) small as the combining condition, text data "Possible blood loss, excessive transfusion, storage of ascites fluid and pleural effusion" is stored as the corresponding message. Thus, the illness information can be displayed on the terminal test device 2 according to the combination of the results of the biochemical test. It should be recognized that this is the same for the treatment information.

In the first to the third embodiments, the information related to the result determination is acquired by transmitting the request information from the terminal test device 2 side to the central device 3, but may be automatically transmitted to the terminal test device 2 at a predetermined timing. In the first to the third embodiments described above, the standard value information is transmitted from the central device 3 to the terminal test device 2 as text data, but image data including the standard value information and the property value information may be created in the central device 3, and transmitted to the terminal test device 2.

Furthermore, in the first to the third embodiments described above, the information related to the result determination is transmitted to the terminal test device 2 and displayed on the display device 25 of the terminal test device 2, but the information related to the result determination is not limited to being displayed at the terminal test device 2 which has transmitted the property value information, and may be displayed on the display device of another computer installed in the same veterinary hospital. This also achieves the aim of assisting the diagnosis of the doctor. In this case, whether or not the computer of the transmission destination is installed in the same facility, veterinary hospital and the like with the terminal test device 2 which has transmitted the property value information is judged, and the information related to the result determination needs to be transmitted only if installed in the same facility, veterinary hospital and the like. Furthermore, in the first to the third embodiments, the central processing device 3 is a server exterior to the facility connected with a plurality of terminal test devices 2 by way of the Internet, but the present invention is not limited thereto, and a server interior to the facility connected with the plurality of terminal test devices 2 in the facility may be applied as the central processing device 3. In this case, an in-facility network such as local area network (LAN) may be used as the network 1. Thus, the risk of the property value information leaking to the outside is alleviated by connecting the central processing device 3 and the terminal test device 2 by way of the in-facility network. Furthermore, since only the property value information of the facility are stored in the property value information storage 341, the number of property value information displayed when browsing the property value information is relatively few, and the target property value information can be easily found. The central processing device 3 may be further connected with the server exterior to the facility.

In the first embodiment, the measurement result (property value information) obtained by measuring the sample in the terminal test device 2 and the attribute information related to the measured sample or the animal which is the collecting source of the relevant sample are corresponded to each other and transmitted to the central device 3. That is, the measurement result (property value information) corresponding to each measurement and the attribute information are transmitted to the central device 3 as one data set, and stored (see FIG. 7). In the second embodiment, the measurement result (property value information) obtained by measuring the sample in the terminal test device 2, the attribute information related to the measured sample or the animal which is the collecting source of the relevant sample, and the correction information used when obtaining the measurement result are corresponded and transmitted to the central device 3, and then stored in the storage device 34 of the central device. That is, the measurement result (property value information) corresponding to each measurement, the attribute information, and the correction information are transmitted to the central device 3 as one data set, and stored in the storage device 34 of the central device 3 (see FIG. 14). However, the respective data configuring one data set does not necessarily need to be stored in the single storage device. For instance, the measurement result (property value information), the attribute information, and the actual data of the correction information may be stored in different storage devices, and the link information to the relevant data may be stored in a table having the data structure shown in FIGS. 7 and 14.

What is claimed is:

1. A system for providing animal test information, comprising:
    test devices for measuring samples obtained from animals; and
    a central device communicably connected to the test devices, the central device being for collecting and processing measurement results acquired by the test devices,
    wherein each of the terminal test devices comprises:
    an input receiving section for receiving input of attribution information of a sample;
    a measurement section for measuring the sample and acquiring a measurement result;
    an information transmitting section for transmitting a data set of the attribution information and the measurement result of the sample to the central device,
    wherein the central device comprises:
    an information receiving section for receiving the data set from each of the test devices;
    a data storage for storing a plurality of the data set;
    a standard value calculation section for calculating a standard value to be used for determining a treatment of an animal, based on a plurality of the measurement result included in a plurality of the data set which have common attribution information.

2. The system for providing animal test information according to claim 1, wherein the attribute information comprises at least one of information related to animal species, information related to breed of the animal, information related to age of the animal, information related to sex of the animal, and information related to type of illness.

3. The system for providing animal test information according to claim 1, wherein
    each of the test devices further comprises a correction information input receiving section for receiving input of correction information for correcting the measurement result, and a measurement result correcting section for correcting the measurement result based on the correction information;
    the measurement result contained in the data set transmitted by the information transmitting section and received by the information receiving section is a measurement result corrected by the correction information;
    the data set further comprises the correction information;
    the central device comprises an original measurement result calculation section for calculating an original measurement result before correction from the corrected measurement result based on the correction information; and
    the standard value calculation section calculates the standard value based on the original measurement result.

4. The system for providing animal test information according to claim 1, wherein the central device comprises a standard value transmitting section for transmitting the standard value with respect to one of the test devices.

5. The system for providing animal test information according to claim 4, wherein
    the central device further comprises a standard value correcting section for correcting the standard value based on the correction information; and
    the standard value transmitted by the standard value transmitting section is a standard value corrected by the standard value information correcting section.

6. The system for providing animal test information according to claim 4, wherein
    each of the test devices comprises a display section for displaying the measurement result and a standard value receiving section for receiving the standard value from the central device; and
    the display section displays information related to the measurement result based on the received data set and the standard value.

7. The system for providing animal test information according to claim 1, wherein the central device further comprises:
    an illness information storage for storing illness judgment condition for judging an illness of the animal based on the measurement result, and illness information indicating the illness presumed when the measurement result corresponds to the illness judgment condition; and
    an illness judgment section for judging whether or not the measurement result corresponds to the illness judgment condition.

8. The system for providing animal test information according to claim 7, wherein the illness information storage stores plural illness judgment conditions and illness information.

9. The system for providing animal test information according to claim 7, wherein the central devices comprises an illness information transmitting section for transmitting the illness information corresponding to the illness judgment condition to one of the test devices when the measurement result corresponds to the illness judgment condition.

10. The system for providing animal test information according to claim 1, wherein the central device further comprises:
    a treatment information storage for storing treatment judgment condition for judging a treatment to be performed on the animal based on the measurement result, and treatment information indicating the treatment presumed when the measurement result corresponds to the treatment judgment condition; and
    a treatment judgment section for judging whether or not the measurement result corresponds to the treatment judgment condition.

11. A method of providing animal test information with a system comprising test devices for measuring samples obtained from animals and a central device communicably connected to the test devices, the central device being for collecting and processing measurement results acquired by the test devices, the method comprising steps of:
    receiving, using a computer processor, input of attribution information of a sample in each of the test devices;
    measuring, using the computer processor, the sample and acquiring a measurement result in each of the test devices;
    transmitting, using a computer processor, a data set of the attribution information and the measurement result from each of the test devices to the central device;

receiving, using a computer processor, the date set from each of the test devices in the central device;

storing, using the computer processor, a plurality of the data set in the central device; and calculating, using a computer processor, a standard value to be used for determining a treatment of an animal, based on a plurality of the measurement result included in a plurality of stored data set which have common attribution information.

12. A system for providing animal test information, comprising:

; and a central device communicably connected to test devices for measuring sample obtained from animals, the central device being for collecting and processing measurement results acquired by the test devices, wherein the central device comprises:

an information receiving section for receiving a data set of attribute information and measurement results from each of the test devices, wherein the attribute information received from the test devices indicates animal species or breed of the animal serving as a collecting source of a sample and the measurement results are acquired by the test devices, a data storage for storing a plurality of the data set, a standard value calculation section for calculating a standard value to be used for determining a treatment of an animal, based on plurality of the measurement result included in a plurality of the data set which have common attribution information; and an information output section for outputting the measurement result and the attribute information included in the data set stored in the data storage.

13. The system for providing animal test information according to claim 12, further comprising the test devices, wherein each of the test devices comprises:

an input receiving section for receiving input of the attribution information indicating animal species or breed of the animal serving as a collecting source of a sample, a measurement section measuring the sample and acquiring the measurement result by using the attribute information received by the input receiving section, and an information transmitting section for transmitting the data set of the attribution information and the measurement result of the central device.

14. The system for providing animal test information according to claim 13, wherein the measurement section measures the sample and acquires an initial measurement result, and acquires the measurement result by correcting the initial measurement result by correction information corresponding to the attribute information received by the input receiving section;

the data set transmitted to the central device by the information transmitting section further comprises the correction information;

the data storage stores the data set comprising the correction information; and the information output section outputs the measurement result, the attribute information, and the correction information stored in the data storage.

15. The system for providing animal test information according to claim 13, wherein the test devices and the central device are connected by way of an in-facility network.

16. The system for providing animal test information according to claim 12, wherein the test devices and the central device are connected by way of Internet.

17. The system for providing animal test information according to claim 16, further comprising a display device for displaying information output by the information output section.

18. The system for providing animal test information according to claim 13, wherein the test devices comprise a first test device for acquiring a measurement result on a first measurement item, and a second test device for acquiring a measurement result on a second measurement item different from the first measurement item.

19. The system for providing animal test information according to claim 13, wherein the test devices are animal blood cell counting devices, and the item of the measurement result comprises at least one of number of white blood cells, number of red blood cells, number of platelets, and hemoglobin content.

20. A method of providing animal test information with a system comprising test devices for measuring samples obtained from animals and a central device communicably connected to the test devices, the central device being for collecting and processing measurement results acquired by the test devices, the method comprising steps of:

receiving, using a computer processor, input of attribution information indicating animal species or breed of the animal serving as a collecting source of a sample in each of the test devices, measuring, using a computer processor, the sample and acquiring a measurement result in each of the test devices, and transmitting, using a computer processor, a data set of the attribution information and the measurement result from each of the test devices to the central device, receiving, using a computer processor, the data set from each of the test devices in the central device, storing, using a computer processor, a plurality of the data set, calculating a standard value to be used for determining a treatment of an animal, based on a plurality of the measurement result included in a plurality of the data set which have common attribution information, and outputting, using a computer processor, the measurement result and the attribute information included in the data set.

* * * * *

UNITED STATES PATENT AND TRADEMARK OFFICE
CERTIFICATE OF CORRECTION

PATENT NO. : 8,086,411 B2
APPLICATION NO. : 12/316306
DATED : December 27, 2011
INVENTOR(S) : Takashi Yoshida et al.

It is certified that error appears in the above-identified patent and that said Letters Patent is hereby corrected as shown below:

<u>In the Claims</u>

In column 25, claim 12, line 12, delete "; and".

In column 25, claim 12, line 14, after "for measuring" replace "sample" with --samples--.

Signed and Sealed this
Tenth Day of July, 2012

David J. Kappos
*Director of the United States Patent and Trademark Office*